United States Patent
Kopesky et al.

(10) Patent No.: US 8,323,718 B2
(45) Date of Patent: *Dec. 4, 2012

(54) CO-PRECIPITATED CARRAGEENAN/XANTHAN GUM COMPOSITIONS AND PROCESSES FOR THEIR PREPARATION

(75) Inventors: Robert Kopesky, Camden, ME (US); W. Preston Brawn, Cherry Hill, NJ (US); Christopher J. Sewall, Hope, ME (US); John Demarco, Jacobstown, NJ (US); James Lamkey, Yardley, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/421,258

(22) Filed: Mar. 15, 2012

(65) Prior Publication Data

US 2012/0171342 A1 Jul. 5, 2012

Related U.S. Application Data

(63) Continuation of application No. 12/108,607, filed on Apr. 24, 2008.

(60) Provisional application No. 60/926,008, filed on Apr. 24, 2007, provisional application No. 60/926,219, filed on Apr. 25, 2007, provisional application No. 60/940,881, filed on May 30, 2007, provisional application No. 61/040,546, filed on Mar. 28, 2008.

(51) Int. Cl.
*A23L 1/06* (2006.01)
*A23K 1/00* (2006.01)

(52) U.S. Cl. ........................ 426/573; 426/615

(58) Field of Classification Search ........................ None
See application file for complete search history.

(56) References Cited

U.S. PATENT DOCUMENTS

| 3,565,539 | A | 2/1971 | La Russa |
| 3,683,789 | A | 8/1972 | Beasley |
| 3,922,357 | A | 11/1975 | Townsend |
| 4,529,585 | A | 7/1985 | Hayes |
| 4,569,838 | A | 2/1986 | De Vries |
| 4,952,686 | A | 8/1990 | Renn et al. |
| 5,498,436 | A | 3/1996 | Modliszewski et al. |
| 5,538,751 | A | 7/1996 | Carter et al. |
| 5,922,391 | A | 7/1999 | Trueck |
| 6,020,012 | A | 2/2000 | Kaufmann et al. |
| 6,159,446 | A | 12/2000 | Randive et al. |
| 6,299,927 | B1 | 10/2001 | Noda |
| 6,479,649 | B1 | 11/2002 | Tsai et al. |
| 6,586,590 | B1 | 7/2003 | Renn et al. |
| 6,610,340 | B1 | 8/2003 | Henson et al. |
| 6,685,978 | B1 | 2/2004 | Hauksson |

(Continued)

FOREIGN PATENT DOCUMENTS

CL 413-01 2/2001

(Continued)

OTHER PUBLICATIONS

Hua et al "Gelling Property of Protein-Gum Mixtures" Food Hydrocolloids Nov. 2003 vol. 17 pp. 889-894.

(Continued)

*Primary Examiner* — Brian Gulledge
(74) *Attorney, Agent, or Firm* — FMC Corporation

(57) ABSTRACT

Co-precipitated carrageenan/xanthan gum compositions and a process for preparation are provided. The compositions are simple to prepare and provide functional performance in a broad range of food, specialty and industrial applications.

14 Claims, 10 Drawing Sheets

U.S. PATENT DOCUMENTS

| | | |
|---|---|---|
| 6,869,632 B2 | 3/2005 | Kaufmann et al. |
| 2002/0019447 A1 | 2/2002 | Renn et al. |
| 2003/0208064 A1 | 11/2003 | Renn et al. |
| 2004/0224075 A1 | 11/2004 | Sugiyama et al. |
| 2005/0031757 A1 | 2/2005 | Boevink |
| 2005/0070704 A1 | 3/2005 | Renn et al. |
| 2005/0118130 A1 | 6/2005 | Utz et al. |
| 2007/0112184 A1 | 5/2007 | Tsai et al. |
| 2007/0275869 A1 | 11/2007 | Hoppe et al. |
| 2008/0085354 A1 | 4/2008 | Paeschke et al. |

FOREIGN PATENT DOCUMENTS

| | | |
|---|---|---|
| CL | 3538-07 | 12/2007 |
| EP | 0068706 A1 | 1/1983 |
| EP | 0266163 A2 | 5/1988 |
| GB | 2137066 A | 10/1984 |
| JP | 2001346527 A | 12/2001 |
| JP | 2001346527 A1 | 12/2001 |
| JP | 2004236654 A1 | 8/2004 |
| JP | 2004350679 | 12/2004 |
| WO | 0174176 A2 | 10/2001 |
| WO | 02072687 A2 | 9/2002 |
| WO | WO-03094638 A1 | 11/2003 |
| WO | WO 2006/127810 A2 | 11/2006 |
| WO | WO-2008086844 A2 | 7/2008 |

OTHER PUBLICATIONS

JP 2001346527 A (machine translation), 2001.

FMC Biopolymer, Product Specification, Gelcarin DX 7150 Stabiliser, Jun. 2000, No. 6387.

FMC Biopolymer, Product Specification, Danagel AF 9050 Stabiliser, Jul. 2000, No. 6289.

FMC Biopolymer, Product Specification, Viscarin SD 2069 Stabiliser, Jul. 2000, No. 6407.

FMC Biopolymer, Product Specification, Gelcarin ME 4951 Stabilizer, Jul. 2000, No. 6817.

Extended European Search Report, Application No. 08746535.7-2114/2136647, PCT/US2008061133, Dated May 24, 2012.

CO-PRECIPITATED CARRAGEENAN/XANTHAN GUM COMPOSITIONS AND PROCESSES FOR THEIR PREPARATION

BACKGROUND OF THE INVENTION

1. Field of the Invention

The present invention is directed to co-processed carrageenan/xanthan compositions, methods of manufacture, and formulations containing such co-processed products.

2. Description of the Related Art

Various hydrocolloids and combinations thereof are known for use in the food industry. Carrageenan-based systems conventionally prepared by admixing crude or purified carrageenan gelling agent with one or more other hydrocolloids or gums are used to provide compositions or gels widely used as thickeners or gelling agents for prepared foods.

Known mixed gel systems intended for use in food or dentifrice applications are commercially dependent on convenient and economical extraction, purification and clarification techniques for obtaining the components substantially free of undesirable impurities and which, upon interaction with a gelling agent, produce clear, stable gels.

U.S. Pat. No. 4,569,838 (de Vries) discloses a dentifrice having desirable rheological properties suitable for facile extrusion from a flexible dentifrice tube. The dentifrice includes a siliceous polishing material, an anti-nucleating agent and a gelling agent mixture of iota-carrageenan and xanthan which is prepared by physical mixing of iota-carrageenan and xanthan.

In the curing of meats, the dressed meat is usually injected with a brine solution, typically by multi-needle injection or by stitch or artery pumping. The injection may be followed by resting, tumbling and/or massaging and finally cooking. Alternatively, the meat may be tumbled or massaged in the brine solution. Some standard pickling procedures are disclosed in U.S. Pat. Nos. 3,565,539; 3,683,789 and 3,922,357.

There is a tendency for the injected brine to leak out of distributed, uncooked food products in either fresh, chilled or frozen condition, during distribution or sale or at the final customer. Thus, there is a need to reduce leakage or liquid seepage from meat products into which brine solution has been incorporated. This tendency may be measured as "drip loss" and may be measured for products which have been specially packaged, e.g. under vacuum or reduced pressure, or for products which have been packaged without vacuum or reduced pressure.

In addition, food products into which brine solutions are incorporated may also suffer from the problem of excess weight loss during cooking. Thus, the incorporated solution may leak out during cooking, creating a higher than acceptable weight loss in the product.

One prior art technique for addressing this problem is to add sodium chloride and/or sodium tripolyphosphates to meat products in order to increase the water-binding capacity of the meats. However, this technique may be undesirable in certain applications due to considerations such as the sodium and phosphate contents of the resultant meat products which may adversely impact their consumer appeal.

In the prior art, it is known to mix brine and gelling polysaccharides such as carrageenan or gellan to provide a solution for injection into food products. U.S. Pat. No. 6,685,978 (Hauksson) discloses a process for forming a food treating composition by mixing water, a gellable polysaccharide and a gelling cation. The gellable polysaccharide may comprises at least one of carrageenans and carrageenans in combination with at least one of locust bean gum, cassia gum, or konjac gum, xanthan gum and xanthan gum in combination with seed gums, meal or flour of seaweeds containing gelling polysaccharides, either treated or untreated. Preferably, the polysaccharide comprises one or more of iota carrageenan, kappa carrageenan, xanthan gum and low ester pectins.

Gelcarin® ME 4951 stabilizer from FMC BioPolymer comprises a mixture of carrageenan and xanthan. This stabilizer is recommended for use in the meat processing industry for injection and tumbling when making cooked ham. Brines made with this stabilizer are said to show little or no sedimentation upon standing without stirring and to result in a decreased cooking loss.

Viscarin® SD 2069 stabilizer from FMC BioPolymer comprises a mixture of xanthan and carrageenan with sugars for standardization. This stabilizer is recommended for use to thicken and stabilize spoonable salad dressings, mayonnaise, sauces and gravies.

Gelcarin® DX 7150 stabilizer from FMC BioPolymer comprises a mixture of carrageenan, calcium lactate, xanthan gum and sugars for standardization. This stabilizer is recommended for use in dry mix cake glazes.

Danagel® AF 9050 stabilizer from FMC BioPolymer comprises a mixture of carrageenan, xanthan and calcium lactate. This stabilizer is recommended for use in specialty fragrance gels with high clarity.

Gelling compositions for food products may be prepared in a number of ways. U.S. Pat. No. 5,498,436 (Modliszewski et al.), for example, discloses a composition comprising: (A) a co-precipitate consisting essentially of: (a) a galactomannan, with (b) a glucomannan, and (B) optionally a gelling agent admixed with the formed co-precipitate. Gelling agents, such as carrageenan may be mixed with the co-precipated product after co-precipitation. Co-precipitation of components (a) and (b) was found to increase the cold solubility of the composition as compared to a physical mixture of the same components.

U.S. Patent application publication no. US 2002/0019447 A1 discloses methods for the clarification of hydrocolloids such as carrageenans and xanthan. In addition, this publication discloses the co-precipitation of a series of hydrocolloid pairs in the examples. A similar disclosure is found in U.S. Patent application publication no. US 2005/0070704 A1.

U.S. Pat. No. 4,952,686 (Renn et al.) discloses soluble cassia alloy gum compositions and processes for making them. One such composition is a co-precipitated combination of cassia gum extract and carrageenan co-precipitated using isopropyl alcohol. The co-precipitated material may be used for absorbing aqueous media.

Despite the foregoing, there remains a need for improved hydrocolloid compositions for use in food and dentifrice products to provide a reduction in leakage or drip loss for injected or tumbled foods, or to improve the rheological properties of a dentifrice.

SUMMARY OF THE INVENTION

Figure 1:
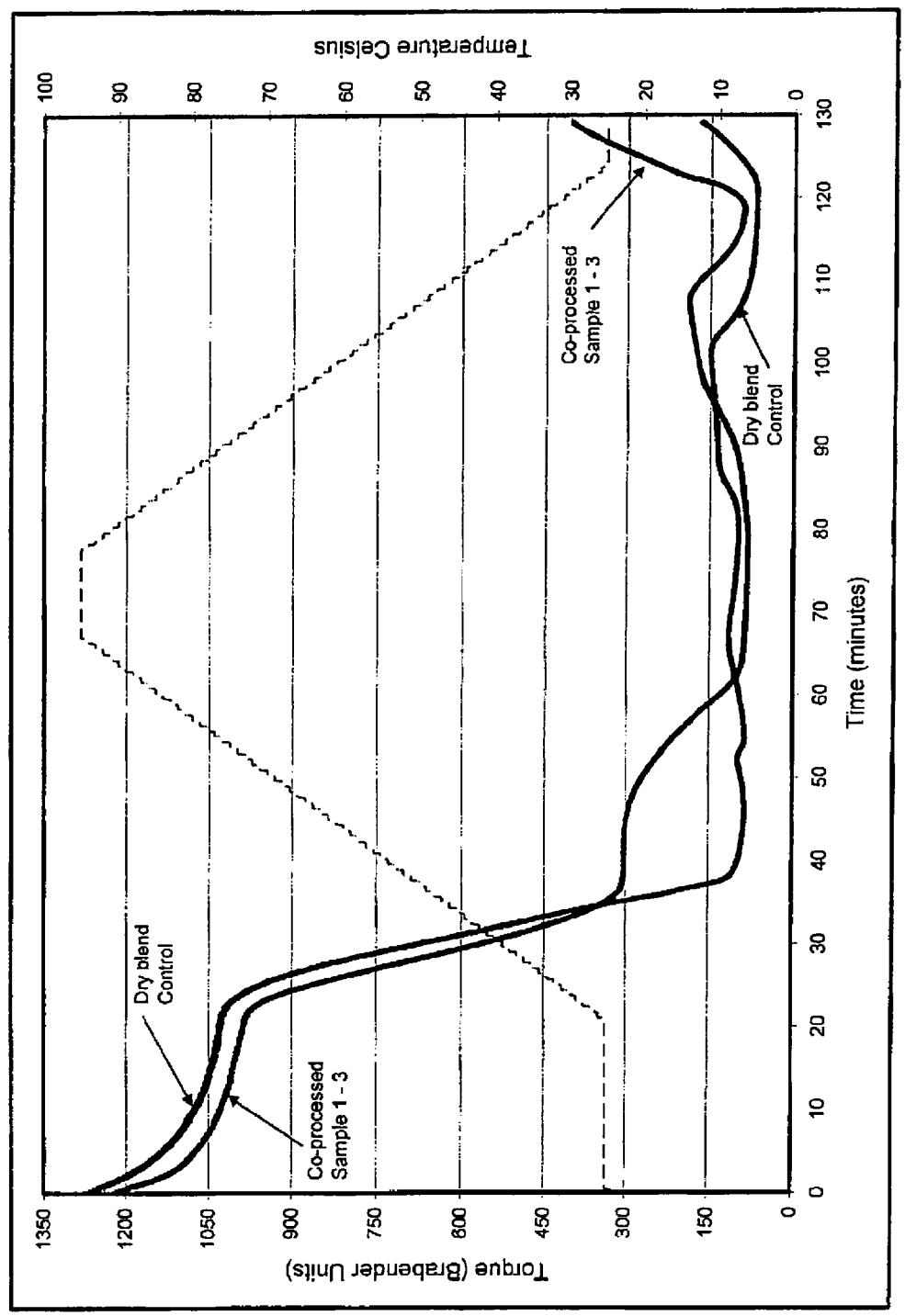
FIG. 1 shows Brabender hydration profiles for aqueous solutions of 2% by weight of 75:25 weight ratio of co-precipitated iota carrageenan/xanthan (Example 1-3) and 2% by weight of a dry blend mixture of 75% iota carrageenan and 25% xanthan (comparative example), respectively.

In a first aspect, the present invention relates to a co-precipitated hydrocolloid composition including at least one carrageenan and at least one xanthan (hereinafter also referred to as "the co-precipitate"). Typically, said carrageenan and xanthan are present in an amount of 60:40 to 95:5, respectively, based on weight percentage. The present invention also relates to compositions containing the co-precipitate.

In a further aspect, the present invention relates to toothpaste compositions including the co-precipitate of the present invention. The toothpaste may include at least one of water, a humectant, a surfactant and an abrasive.

In another aspect, the present invention relates to a dry composition including the co-precipitate of the present invention and at least one additional hydrocolloid.

In a further aspect, the present invention relates to a process for preparing a co-processed hydrocolloid including the steps of mixing hydrated hydrocolloids including at least one carrageenan and at least one xanthan, and co-precipitating the mixed hydrocolloids to recover a co-precipitated hydrocolloid from the aqueous medium.

In another aspect, the present invention relates to a process for treating an uncooked food product comprising at least one of meat, seafood and poultry, comprising the step of adding to the uncooked food product an aqueous composition comprising the co-precipitate.

In another aspect, the present invention relates to a food product made by adding to an uncooked food product comprising at least one of meat, seafood and poultry, an aqueous composition comprising the co-precipitate.

These and other aspects of the present invention will be apparent from the detailed description of embodiments of the invention and the examples which follow.

DETAILED DESCRIPTION OF EMBODIMENTS OF THE INVENTION

The co-precipitated hydrocolloids described herein contain two or more chemically different hydrocolloids, one of which is a carrageenan and another of which is a xanthan gum. These hydrocolloids are preferably prepared in a manner which produces a substantially homogeneous product, as distinguished from a two component physical mixture ("dry blend") of a carrageenan and a xanthan gum. A substantially homogeneous co-precipitated carrageenan/xanthan product may have some minor variations in the relative concentrations of the two co-precipitated components at particular locations in the product and the product cannot be mechanically separated into individual components.

Carrageenan (also called carrageenan gum) is a commercially significant galactan polysaccharide found in red seaweed. All carrageenans contain repeating galactose units joined by alternating $\alpha 1 \rightarrow 3$ and $\beta 1 \rightarrow 4$ glycosidic linkages and are sulfated to widely varying degrees. The types of carrageenan may be distinguished, in part, by their degree and position of sulfation, as well as the seaweed from which they are obtained. The various types of carrageenan include kappa, kappa-2, iota, lambda, mu and nu. Because carrageenans vary in their composition and structure, they are known to vary in properties and uses. Carrageenans also vary in molecular weight, cation content and cation type.

Carrageenan is a hydrocolloid which may consist of one of more of the potassium, sodium, magnesium, calcium, zinc and ammonium sulfate esters of galactose and 3,6-anhydro-galactose copolymers. These hexoses are alternately linked $\alpha$-1,3 and $\beta$-1,4 in the polymer. The relative proportions of cations existing in carrageenan may be changed during processing.

Since carrageenans are known to have varying properties, the type of carrageenan used for a particular product may be selected based on the desired end use and the properties of the carrageenan suitable or desirable for that end use. For example, different carrageenans gel with different salts allowing some customization of the materials in situations where gelation is desirable.

Xanthan (also called xanthan gum) is a microbial exopolysaccharide produced by the naturally occurring bacterium Xanthomonas campestris. It is a widely used biopolymer in the food and pharmaceutical industries. It is also used in many other fields such as petroleum production, pipeline cleaning, enhanced oil recovery, textile printing and dyeing, ceramic glazes, slurry explosives and in cosmetics and oral care. Xanthan is typically used for the purposes of thickening, suspending, stabilizing and gelling.

Xanthan consists of a pentasaccharide repeating subunit. It consists of two D-glucopyranosyl units, two D-mannopyranosyl units and a D-glucopyranosyluronic acid unit as determined by methylation analysis and uronic acid degradation. The molecule has a (1,4) linked ($\beta$-D-glucopyranosyl backbone as found in cellulose, with a tri-saccharide side-chain attached to the O-3 position on alternate glucosyl units. The side chain is constructed such that the D-glucuronosyl unit is flanked by the two mannosyl units. Approximately half of the terminal D-mannosyl units have a pyruvic acid moiety across the O-4 and O-6 positions. The other D-mannosyl unit is substituted at the O-6 position with an acetal group. Xanthan is available readily as the sodium or potassium salt, or as mixtures of sodium, potassium or calcium salts, and at varying levels of pyruvate. Xanthan has been estimated to have a molecular weight between 2 million to 50 million Daltons. This wide range of values is believed to be due to polymer chain association.

Co-processing is done by a method of co-precipitation of a carrageenan and a xanthan. The co-processing method typically includes the steps of: (A) mixing a carrageenan, or seaweed containing carrageenan, with an aqueous medium (optionally accompanied by heat and/or agitation, and/or alkali) to form a carrageenan sol containing hydrated carrageenan; (B) mixing xanthan in a similar manner with the same aqueous medium as the carrageenan in (A), or in a separate aqueous medium, to form a xanthan sol containing hydrated xanthan; and, if the carrageenan sol and xanthan sol were prepared separately, co-mixing the carrageenan sol and xanthan sol to form a co-mixture of hydrated carrageenan and hydrated xanthan; (C) optionally clarifying the carrageenan sol, the xanthan sol, or the co-mixture of hydrated carrageenan and hydrated xanthan to remove insoluble solids; (D) optionally concentrating the solids of the co-mixture of hydrated carrageenan and hydrated xanthan by any effective means, such as evaporation or ultrafiltration; (E) co-precipitating the co-mixture of hydrated carrageenan and hydrated xanthan to form a co-precipitate, preferably by the addition of an organic solvent that is miscible with the aqueous medium, or other effective precipitation means; (F) separating the co-precipitate from the aqueous medium; (G) drying the co-precipitate, and (H) optionally grinding the dried co-precipitate to a finer powder.

The total solids concentration during co-processing, and the temperature of processing, may vary according to tradeoffs known in the art. Higher solids concentrations and lower processing temperatures are advantageous in increasing process efficiency, but the same conditions raise the viscosity of the solution and make processing more difficult. The optimal balance depends on the details of the processing equipment used. In general, a maximum total concentration of the carrageenan and xanthan in the processing medium, on initial mixing to form the co-mixture, of no more than about 10.0 wt %. A concentration of 1.0 to 3.0% is recommended for optimum processing, and a maximum total gum concentration range of from about 1.5 to 2.5 wt % is often preferable. Where a clarified co-precipitate is desired, it is of particular importance to adjust the total solids content of the processing medium to facilitate filtration of the co-mixed sols; a total solids content of 0.5 to 3.0%, more preferably, from about 1.0 wt % to about 2.0 wt % is desirable for ease of processing when clarification is desired. Processing is dependent on the viscosity of the co-mixture and the gelling temperature of the co-mixture. Some embodiments allow for higher solids concentrations of up to 10% during processing, by lowering molecular weight or reducing the level of cations that may contribute to gelation.

The co-precipitation of the carrageenan and xanthan is critical to this invention, however, the co-precipitation step may be carried out by any effective means which provides a substantially homogenous precipitate and does not result in significant isolation and separation of one of the carrageenan and xanthan components. Examples of suitable co-precipitation means include co-precipitation by use of organic solvents, drum drying, spray drying, air drying, fluid bed drying and freezing followed by pressing or drying. Co-precipitation drying methods are preferred. Co-precipitation with a water-miscible solvent and possible pH adjustment is even more preferred. Co-precipitation with alcohols, and especially with isopropyl alcohol, is the most preferred co-precipitation method.

The amount of alcohol solution sufficient for co-precipitation will vary with the co-precipitation conditions, but addition of two or more parts of isopropyl alcohol (at about 65-85% isopropyl alcohol) to one part of the co-mixture solution is an effective precipitant. Lower ratios of alcohol solution to co-mixture may be effective, depending on details of the process conditions, such as gum concentration and temperature. Lower addition ratios, such as 1.5 parts of alcohol solution to 1 part of co-mixture, or 1 part of alcohol solution to 1 part of co-mixture are preferred when effective for co-precipitation. The carrageenan can comprise from 1 wt % to 99 wt % of the co-precipitate (based on gum solids), but usually comprises about 50 wt % to 90 wt %, preferably 60 wt % to 80 wt % of the co-precipitate, and in some more preferred embodiments the carrageenan comprises 70 wt % to 80 wt % of the co-precipitate, based on the total dry weight of the polysaccharides contained in the co-precipitate.

In one embodiment, the present invention relates to co-precipitate compositions consisting essentially of the co-precipitated carrageenan/xanthan. In another embodiment, the present invention relates to compositions consisting of the co-precipitated carrageenan/xanthan. Preferred compositions of these embodiments have carrageenan/xanthan weight ratios of 60:40 to 95:5. More preferred compositions have carrageenan/xanthan weight ratios of 60:40 to 90:10, even more preferably, the compositions have carrageenan/xanthan weight ratios of 70:30 to 80:20, with a most preferred weight ratio being 75:25. These co-precipitate compositions may optionally be clarified.

The co-precipitated carrageenan/xanthan (also referred to herein as "the co-precipitate") is suitable for use as a binder, a suspending agent and/or a thickening agent. It is also suitable for use in a dry mix or as a readily dispersing component in dry blends. One advantage of the co-precipitates of the invention is that they are suitable for use over a wide pH range. The pH range over which the co-precipitated carrageenan/xanthan product may be used includes acidic, basic and neutral conditions, for example, from about pH 2.0 to about pH 11.

The co-precipitated carrageenan/xanthan can be used in formulations and may be combined with one or more additional hydrocolloids including xanthan, carrageenan and carboxymethyl cellulose. The present invention also encompasses compositions containing the co-precipitated carrageenan/xanthan.

Suitable uses for the co-precipitated carrageenan/xanthan or compositions containing the co-precipitates are in food, cosmetic, pharmaceutical, industrial and specialty applications. Certain preferred applications include food and oral care applications where it is useful as a stable thickener in high ionic environments.

The co-precipitates or compositions containing the co-precipitates are useful as the base for many food and industrial products such as: a gelled or thickened food; a pourable salad dressing; a liquid food or food additive; a food spread such as a margarine or cheese spread; a water dessert gel; a jam or jelly; a confection; a mayonnaise; a frozen dessert; a cosmetic or pharmaceutical liquid; an excipient for use as a binder or disintegrant; a cream or lotion excipient; a dental care product; an air freshener gel; a de-icing fluid; and the like. Where the compositions are used as water dessert gels, they may be in dry form as a mix, or may be in the form of aqueous gels, with or without the admixed gelling agent. The compositions are typically used in admixture with one or more flavorants, colorants, sweeteners, food particles, herbs, preservatives, buffering agents, acidifying agents or gel strengtheners.

Food compositions in which the co-precipitates or compositions containing the co-precipitates may be employed include meat (beef, chicken, pork), fish and protein-based products, beverages, dairy products, water dessert gels, frozen desserts including ice creams, frozen yogurts, and novelties, food spreads, pourable or spoonable salad dressings, soups, sauces, and gravies, acidified foods and acidified beverages, seasonings such as rubs, marinades and spice blends, gelled foods and thickened foods.

Industrial compositions in which the co-precipitates or compositions containing the co-precipitates may be employed include oil field drilling and fracture fluids, cements, wall plasters, pesticides, herbicides, pet foods, cleaning and sanitizing compositions and deicing fluids.

Personal Care compositions in which the co-precipitates or compositions containing the co-precipitates may be employed include, for example oral care products, toothpastes, air freshener gels, cosmetic creams and lotions.

Dry blend compositions in which the co-precipitates may be employed include compositions comprising the co-precipitate and one or more salts including but not limited to sodium, calcium or potassium salts, salts of chlorides, lactates, phosphates, citrates and carbonates such as sodium carbonate.

Salts, sugar, dextrose, silica, and maltodextrin may be used as standardizing agents for the co-precipitates and compositions containing the co-precipitate, as well as in the dry blend compositions. Typically, such compositions are standardized for viscosity and/or gel strength to ensure consistency as delivered to the customer since the properties of such products may vary due to the fact that they are obtained from natural sources, for example.

The co-precipitates or compositions containing the co-precipitates may optionally be admixed with at least one compound selected from the group consisting of celluloses, chemically-modified celluloses, seaweed products, natural gums, biosynthetic gums, proteins, synthetic hydrocolloids, starches, modified starches, dextrins, dextrose, sugars, surfactants, emulsifiers and salts. Similarly, dry blend compositions in which the co-precipitates may be employed may contain one or more of these additional ingredients. A preferred dry blend composition contains the co-precipitate in combination with an additional hydrocolloid which may be selected from carrageenan, xanthan, carboxymethyl cellulose and mixtures thereof.

When the compositions containing the co-precipitate are foods, industrial, pharmaceutical or personal care products, then the compositions may contain at least one material selected from the group consisting of clays, preservatives, metal oxides, colorants, acidulates, buffers, food particles, herbs, acidifying agents, gel strengtheners, modifiers, emulsifiers, proteins, polypeptides, proteins, amino acids, cultures, and mixtures thereof and optionally a hydrocolloid.

The present invention also includes toothpastes and binder formulations containing the co-precipitated carrageenan/xanthan for use in toothpastes. Suitable toothpastes may contain one or more of an abrasive or polishing agent, a humectant, a binder, a surface active agent, water, and, optionally, other materials that are conventional components of toothpaste compositions, such as flavors and sweeteners. The solid and liquid components of a toothpaste composition are formulated to produce a product that is a consistent, extrudable, creamy material.

The binder builds viscosity, provides a desirable consistency and thixotropy, and prevents separation of the ingredients during storage and use. The binder includes the co-precipitated carrageenan/xanthan composition of the present invention and optionally additional hydrocolloids such as cellulose derivatives ("cellulose gums") including, for example, carboxymethyl cellulose (CMC), methyl cellulose, hydroxyethyl cellulose, hydroxypropyl methyl cellulose, and mixtures thereof; polyvinyl pyrrolidone; xanthan; carrageenans such as iota carrageenan, kappa carrageenan, kappa-2 carrageenan, lambda carrageenan, and mixtures thereof; guar gum; gum karaya; gum arabic; gum tragacanth; and mixtures thereof.

Carrageenan containing toothpaste is disclosed in Randive, U.S. Pat. No. 6,162,418, incorporated herein by reference. Hydrated silica and colloidal silica may be used as thickeners. Silica thickeners are disclosed, for example, in Niemi, U.S. Pat. No. 6,342,205, incorporated herein by reference.

The vehicle of the toothpaste composition is orally acceptable and is comprised of water and a humectant. The humectant provides mouthfeel and also prevents the toothpaste composition from drying out. Typical humectants are polyols of three to six carbons in which each carbon is hydroxylated, and mixtures thereof, such as glycerol (glycerin), sorbitol, polyethylene glycol, polyoxyethylene glycol, mannitol, xylitol, and other sugar alcohols. Sorbitol and glycerol are preferred. The water is preferably deionized and free of impurities.

Toothpaste compositions also comprise a surface active agent to emulsify or otherwise uniformly disperse toothpaste components. The surface active agents are typically anionic or nonionic surface active agents, or mixtures thereof. Examples of suitable surface active agents include water-soluble salts of higher fatty acid monoglyceride monosulfates; higher alkyl sulfates; higher alkyl aryl sulfonates; higher alkyl sulfoacetates; higher fatty acid esters of 1,2 dihydroxy propane sulfonate; substantially saturated higher aliphatic acyl amides of lower aliphatic amino carboxylic acid compounds, such as those having 12 to 16 carbon atoms in the fatty acid, alkyl or acyl radicals; higher olefin sulfonates, higher alkyl poly-lower alkoxy (of 3 to 100 alkoxy groups) sulfates, and fatty acid soaps. Examples of these anionic surface active agents include sodium lauryl sulfate (SLS), sodium hydrogenated coconut oil fatty acids monoglyceride monosulfate, sodium dodecyl benzene sulfonate, sodium lauryl sulfoacetates, sodium N-lauryl sarcosinate, and sodium cocate. Suitable types of nonionic surface active agents include chains of lower alkyene oxides such as ethylene oxide and propylene oxide. A commonly used surface active agent is sodium lauryl sulfate.

The toothpaste composition may comprise a number of other optional ingredients. Agents that provide therapeutic or cosmetic benefits may be present, such as enamel hardening agents, tartar control agents, whitening agents, and antibacterial agents. One or more sweeteners and flavorings may be added for consumer satisfaction. Other materials that are conventional components of toothpaste compositions, such as opacifiers and colorants, may also be present.

Examples of flavorings (flavors, flavoring materials, or flavoring agents) include: menthol; carvone; anethole; methyl salicylate; and the oils of spearmint, peppermint, wintergreen, sassafras, clove, sage, eucalyptus, marjoram, cinnamon, lemon, lime, grapefruit, kumquat, tangerine, and orange. Examples of sweeteners (sweetening agents) include sucrose, lactose, maltose, sorbitol, xylitol, sodium cyclamate, perillartine, L-aspartyl-L-phenylalanine methyl ester (aspartame), and saccharine.

Pyrophosphate salts having anti-tartar efficacy such as a di-alkali or tetra-alkali metal pyrophosphate salts such as $Na_4P_2O_7$ (TSPP), $K_4P_2O_7$, $Na_2K_2P_2O_7$, $Na_2K_2H_2O_7$, and $K_2H_2P_2O_7$, long chain polyphosphates such as sodium hexametaphosphate, and cyclic phosphates such as sodium trimetaphosphate may be present in the toothpaste composition. Examples of hardening agents are fluoride salts such as sodium fluoride, potassium fluoride, calcium fluoride, zinc fluoride, stannous fluoride, zinc ammonium fluoride, sodium monofluorophosphate, potassium monofluorophosphate, and laurylamine hydrofluoride.

Antibacterial agents may also be included in the toothpaste compositions. Especially useful are non-cationic antibacterial agents that are based on phenolic and bisphenolic compounds, halogenated diphenyl ether, benzoate esters and carbanilides, such as sodium benzoate; 4-chlorophenol, 2,2'-trichloro-2-hydroxy-diphenyl ether(triclosan); esters of p-hydroxybenzoic acid, especially the methyl, ethyl(ethyl parasept), propyl(propyl parasept), butyl(butyl parasept), and benzyl esters; 3,4,4'-trichlorocarbanalide and 3,3',4-trichlorocarbanilide. A preferred antimicrobial agent is triclosan(5-chloro-2-(2,4-dichlorophenoxy)phenol). Nonionic antimicrobial agents such as sesquiterpene alcohols such as merolidol and bisabolol are also useful.

Whitening agents may be present in the toothpaste composition. Useful whitening agents are oxidizing agents such as calcium peroxide, urea peroxide, peracetic acid, and sodium percarbonate. An opacifier, such as titanium dioxide, may be added to make the toothpaste opaque or to increase its opacity.

The toothpaste composition may also comprise other ingredients that are conventional components of toothpaste compositions, including, for example, desensitizing agents for sensitive teeth such as sodium nitrate; orally acceptable colorants such beta-carotene, chlorophyllin, FD&C Yellow #5, FD&C Yellow #6, FD&C Blue #2, FD&C Red #4, FD&C Green #6, FD&C Yellow #10, FD&C Red #40, D&C Green #5, D&C Red #30 lake, and FD&C Blue #1 lake; healing agents, such as rose-seed oil; chelating/sequestering agents, such as citrates; vitamins, such as vitamin C and vitamin E; amino acids; proteins; antibiotics; anti-enzymes; enzymes; pH control agents (buffers); antioxidants; and preservatives.

The toothpaste composition typically comprises about 0.05 wt % to 3.0 wt % of the binder containing the co-precipitated carraeenan/xanthan, based on the total weight of the toothpaste composition.

Processes for preparing low carrageenan toothpastes are disclosed in Ballard, U.S. Pat. No. 6,187,293, incorporated herein by reference.

High moisture toothpastes are also known. The amount of water present in a "high moisture toothpaste compositions" depends to some extent on the abrasive used in the toothpaste compositions. Higher levels of calcium based abrasives, such as dicalcium phosphate and calcium carbonate, and lower levels of silica are used in toothpaste compositions. Therefore, a silica-based high moisture toothpaste composition will typically comprise more water than one that comprises a calcium based abrasive. High moisture toothpastes that comprise iota carrageenan as the binder, and their preparation, are described, for example, in Randive, U.S. Pat. No. 6,159,446, incorporated herein by reference.

Silicon dioxide or silica's may be used in a toothpaste composition for its abrasive properties or for its thickening properties. Examples of types of silica's used as abrasives are Zeodent® 113 and Zeodent® 124 (J.M. Huber Co., Atlanta, Ga., USA). Examples of silicas used as a thickener are Zeodent®, 165, Zeodent® 163, and Zeodent® 153 (J.M. Huber Co., Atlanta, Ga., USA). The difference in properties between these two types of materials is given in Niemi, U.S. Pat. No. 6,342,205, especially in Tables B and C, and the disclosure that accompanies these Tables. The disclosure of U.S. Pat. No. 6,342,205 is incorporated herein by reference.

Gadkari in WO2004071321 discloses high moisture, low abrasivity toothpastes that contain microcrystalline cellulose and less than 8 wt %, typically 7 wt % or less, more typically 1 to 7 wt %, of silica thickener. This toothpaste composition has lower abrasivity than toothpaste compositions that comprise 8 wt % to 15 wt % silica thickener. In addition, the toothpaste composition comprises less that 15 wt %, 1 wt % to less than 15 wt %, in some cases 6 to 10 wt %, of silica abrasive. The total amount of silica present is 2 to 22 wt %, in some cases 8 to 18 wt %, and in other cases 10 to 14 wt %.

In high moisture toothpastes, water comprises 45 to 70 wt % of the high moisture silica containing toothpaste composition. The water content may also be 50 to 70 wt % or 60 to 70 wt %, based on the total weight of the toothpaste composition.

The "as made" viscosity (i.e., the viscosity of the toothpaste composition after cooling to ambient temperature but before standing for more than several hours, or the "initial viscosity") of the toothpaste composition is typically less than 200 mPa-s to avoid sedimentation and to make the composition convenient for use in automated filling equipment.

When dicalcium phosphate (DCP) is used as the abrasive, the toothpaste composition typically comprises about 25 to 55 wt %, more typically about 35 to 53 wt % of dicalcium phosphate. When calcium carbonate is used as the abrasive, the toothpaste composition typically comprises about 25 to 55 wt %, more typically about 35 to 50 wt %, of calcium carbonate. Thus, because of the higher level of abrasive in the toothpaste composition, the amount of water in these high moisture toothpaste compositions will be less than in one that contains silica. These high moisture toothpaste compositions contain 35 to 60 wt % water and preferably 40 to 60 wt % water. The binder comprises the co-precipitated carrageenan/xanthan, optionally formulated with a cellulose gum, preferably carboxymethyl cellulose, typically at a binder content about 0.5 to 3.0 wt % in the toothpaste composition. The amount of binder may be reduced by the presence of a silica thickener, for example up to about 7 wt %, such as 1.0 to 7.0 wt %, typically about 1.0 to 4.0 wt % of a silica thickener, or by the presence of silica thickener and microcrystalline cellulose, for example, 0.5 to 7.0 wt %, typically 0.5 to 2.0 wt % of the silica thickener and 0.5 to 10.0 wt %, typically 1.0 to 3.0 wt % of non-colloidal microcrystalline cellulose, colloidal microcrystalline cellulose, or a mixture thereof. After the abrasive, the water, the binder, and the other ingredients, have been accounted for, humectant accounts for the balance of the material.

The toothpaste composition typically comprises about 0.8 to about 3.0 wt %, preferably about 1.0 to about 2.0 wt %, of the surface active agent. When a flavoring is present, the toothpaste composition typically comprises about 0.1 to about 2.0 wt %, more typically about 0.5 to about 1.5 wt %, of the flavoring. When a sweetener is present, the toothpaste composition typically comprises about 0.1 to about 2 wt % of the sweetener. When an anti-tartar agent is present, the toothpaste composition typically comprises about 0.5 to about 8.0 wt % of the anti-tarter agent. When an anti-bacterial agent is present, the toothpaste composition typically comprises about 0.03 to about 1 wt % of the antibacterial agent. When a whitening agent is present, the toothpaste composition typically comprises about 0.1 to about 5 wt %, preferably about 0.5 to about 2 wt %, of the whitening agent. When a pyrophosphate salt is present, the toothpaste composition typically comprises about 0.5 to about 8.0 wt %, preferably about 1.5 to about 3 wt %, of the pyrophosphate salt. When a hardening agent is present, the hardening agent typically comprises about 0.1 to about 5 wt % of the toothpaste composition. When present, other ingredients, such as dyes and opacifiers, are present in effective amounts, that is, each ingredient is present in the amount necessary to achieve its particular purpose.

The toothpaste compositions can be prepared using either the hot process or the ambient process, and either a batch process or a continuous process may be used. The ambient process is sometimes called the cold process. The hot process is described, for example, in Scott, U.S. Pat. No. 4,353,890, Mulvey, U.S. Pat. No 4,565,692, and Ballard, U.S. Pat. No. 6,187,293, the disclosures of which are incorporated herein by reference. A continuous process for the manufacture of toothpaste is disclosed, for example, in Ballard, U.S. Pat. No. 6,187,293, especially in FIG. 1 and the accompanying text, the disclosure of which is incorporated herein by reference. A continuous process for the manufacture of toothpaste is also disclosed in Catiis, U.S. Pat. No. 5,236,696.

Those skilled in the art will recognize that the co-precipitated carrageenan/xanthan of the present invention is suitable for use in toothpaste binders, alone or in admixture with additional hydrocolloids, for the manufacture of a wide variety of oral care products including opaque, hot process, high moisture, high moisture low abrasive, clear, and striped toothpaste formulations.

The present invention also relates to food treating compositions. Food products treated in accordance with to the present invention can be prepared with the food treating composition of the present invention at one location and shipped to another location, with reduced liquid seepage, leakage or drip loss, for further processing. This is a significant advantage since the consumer appeal of such products may be adversely affected by the presence of liquid in the meat packaging. In addition, liquid seepage into the meat packaging may provide a suitable environment for growth of harmful microbes and thus should be avoided for this additional reason.

Freshly processed meats may be injected with a brine solution containing co-precipitates in accordance with the present invention. The present invention may be used to improve brine retention by 25 to 50% over phosphate and standard carrageenan systems in fresh poultry or pork and to reduce purge in packages. In addition, the co-precipitates of the present invention exhibit an excellent tolerance for salts and thus can be added to the brine solution or other compositions before or after the salts are added without an adverse performance impact. This simplifies processing and eliminates the potential for errors in formulation of products.

Brine solutions may be made in any suitable conventional manner. Ingredients included in the brine solutions may be added in any suitable form including as a dry blend or dry mix. Sodium chloride and/or tripolyphosphate may be added to the brine to increase the water binding capacity of the meat. As demonstrated herein, the present products are effective in brine solutions with or without phosphates and thus can be employed in products where eliminating phosphates is a priority.

Moreover, the food treating composition of the present invention permits the food to be frozen for subsequent thawing reduced liquid seepage, leakage or drip loss when thawing. Still further, the food treating composition according to the present invention permits the cooking of food with reduced weight loss during cooking to provide an improved cooking yield. This leads to improved product moisture retention in food service applications By "uncooked food product" is meant a food product, which has not received a heat treatment, or has received a heat treatment at one or more temperatures below the temperature, which renders the proteins in food denatured. This temperature is typically below about 60° C., but varies according to the protein composition of the food. For meat and poultry, the heat treatment would comprise one or more temperatures of preferably less than about 60° C., and even more preferably less than about 55° C. For fish, the heat treatment would comprise one or more temperatures of preferably less than about 50° C., and even more preferably less than about 40° C. Thus, uncooked food product includes food product that is uncooked, such as food product that has not being subjected to any treatment temperature, such as chilled or frozen food product, as well as food that has been heated, but not heated sufficiently to arrive at a protein denaturing temperature, such as semi-warm smoking. Preferably, the food treating composition according to the present invention is added at temperatures at which food products are normally processed, handled, shipped and/or stored.

The co-precipitate composition or compositions containing the co-precipitate can be added to the food product using injection equipment, mixing, blending, and tumbling equipment. Once the composition is in the food product, it can absorb water, thicken or gel to provide an advantageous reduction in seepage, leakage or drip loss of liquids from the food product.

Other potential advantages which may be achieved using certain brine formulations in accordance with the present invention include improved consistency of injected meat products thereby reducing gel pocket formation and increasing permeation into meat for better distribution. These advantages may flow from the ability to provide relatively low viscosity brines using the co-precipitates of the present invention. This also may lead to a reduced potential for blow outs and muscle tears in the meat products since the lower viscosity brine is less likely to exert localized high forces on the meat products during injection. It is also expected that the low viscosity brines of the present invention will improves pumpability, reduce equipment wear and increase throughput.

If injection equipment is utilized to add the composition to the food product, the viscosity of the composition is preferably suitable for injection using conventional injection equipment, such as a Fomaco Multineedle Injector Equipment model FGM 20/40. For example, it is preferred that the composition have a viscosity of about 1 to 1000 cps, about 5 to 800 cps, about 10 to 800 cps and, most preferably, about 20 to 800 cps. In instances where the composition is to be mixed with the food, such as in high shear equipment, the viscosity of the composition can be higher. Thus, if the incorporation of the composition will take place in a grinder, cutter or emulsifiers, e.g. colloid mills, then higher concentrations of the co-precipitate can be utilized to provide higher viscosity compositions. As discussed above, the concentration of polysaccharide included in the food treating composition can be varied depending upon the manner of addition to the food product, and can also be varied depending upon the specific co-precipitate or composition containing the co-precipitate utilized in the composition. If the composition is to be added using injection equipment, then it is preferred that the co-precipitate be included in the brine composition at a concentration that permits the use of injection equipment, such as up to about 5 wt %, more preferably about 0.01 to 2 wt %, more preferably about 0.1 to 1 wt %.

The co-precipitate or composition containing the co-precipitate is preferably not gelled during preparation, but could potentially be gelled in situ after incorporation into the food product. Thus, typically the brine composition includes the co-precipitate, but does not include components therein that cause gelling of the composition at the time of preparation and/or is not prepared at conditions that enable the composition to gel. For example, the brine composition can contain components that would, under certain conditions, influence gelling of the co-precipitate composition; however, these components are present under conditions that do not enable them to gel the solution. Thus, the components may be undissolved, such as insoluble at the particular temperature or pH, such as some poorly soluble calcium salts, including calcium sulphate. The components may be in an inactive form during the preparation of the composition, such as present in the composition as an encapsulated active ingredient which will become active only at a particular temperature or pH.

The food treating compositions of the present invention may optionally be gelled in a food product, if desired. After addition to the food product, depending upon the particular composition of the co-precipitate, conditions could be present in the food product and/or conditions may be modified in the food product to cause gelling of the composition within the food product, if desirable, though gelation may not be necessary to achieve the desired improvements in the food product. For example, gelation could occur during cooking, in which case the gel may add some viscosity, and thereby partially reduce cooking loss. Thus, liquid seepage or drip loss from the food product may be reduced during cooking as well as during distributing and handling to provide higher cooking yields.

The food products can be any type of meat, poultry or seafood, from wild or domesticated animals with or without bones or skin, whole or in parts, minced, comminuted or emulsified, in any state of natural, fresh, chilled frozen and jerked meats, or in another condition, which is un-cooked.

The invention will now be described with respect to certain examples which are merely representative of the invention and should not be construed as limiting thereof.

Test Methods

Viscosity: A 1.5% by weight aqueous solution of the carrageenan/xanthan sample are prepared by mixing and heating to 85° C., holding for 15 minutes, and then cooling to 75° C. before measuring the viscosity using a Brookfield LV viscometer. The viscosity was measured using an aqueous solution containing 1.5% by weight of carrageenan or 1.0% by weight of xanthan following the same method unless otherwise stated.

Moisture content is determined by weight loss upon drying for 1 hour at 110° F. in a oven.

Gel strength—Gels are prepared by heating the solution in a boiling water bath with continuous mechanical agitation to a temperature of 82° C. The weight is adjusted for evaporative losses using distilled water and the solution is well mixed. The hot solution is poured into three dishes (70 mm×50 mm) and placed in a 25° C. water bath for one hour. The gels are inverted and placed in the test instrument so that the plunger will contact the center of the gel. The break force strength (in grams force) and the penetration distance (in centimeters) of the probe are determined using an Instron Materials testing instrument Model 4442, 10 kg capacity, with a 10.9 mm diameter tapered metal plunger at a descent speed of 70 mm/minute Water gel compositions for testing include a 2% water gel which uses 2% by weight of gum solids in distilled water; a "1%+1" water gel which uses 1% by weight of gum solids plus 1% by weight of potassium chloride in distilled water and a "1%+1+1" water gel which uses 1% by weight of gum solids plus 1% potassium chloride and 1% by weight of calcium chloride in distilled water. Milk gels are prepared by mixing the sample in cold, homogenized, whole milk and heating to 82° C. After adjusting for evaporative losses, the hot solution is poured into dishes and placed in a 10° C. water bath for one hour prior to gel strength testing with the Instron Model 4442 as for water gels except that a 21.5 millimeter diameter tapered metal plunger is used.

Acid stability: A 1.5% solution was made with mixing and heating to 82° C. followed by cooling to 75° C. The sample was placed in a bath at 75° C. and 5.04 grams of sodium phosphate and 6.2 grams of sodium citrate were stirred in. The viscosity was measured (time 0) using a Brookfield LV viscometer at 30 rpm. The viscosity and pH (=3.8) were re-tested after 7.5, 15, 30, 45, 60, 75 and 90 minutes at 75° C. The rate of hydrolysis is calculated as the decrease in viscosity per minute.

Particle size was measured using a Horiba LA-910 laser scattering particle size analyzer.

Brabender testing: The hydration and viscosity behavior of co-precipitated carrageenan/xanthan in aqueous solution or in product formulations are measured using a Brabender viscometer (model Viskograph-E). The sample is stirred while heated, held at a maximum temperature, and then cooled. The heating and cooling rates are set at 1.5° C./minute. The cup rotational speed on the Brabender viscometer is set at 75 rpm. Brabender hydration profiles are determined using a 2 wt % sample in de-ionized water. The test solution uses the following heating/cooling profile: hold for 20 minutes at 25° C., heat to 95° C., hold at 95° C. for 10 minutes, cool to 25° C., and hold at 25° C. for 5 minutes. The hydration is also characterized in a model toothpaste elixir containing de-ionized water (42.8 wt %), sorbitol (33.1 wt %), glycerin (19.5 wt %), sodium monofluoro phosphate (2.1 wt %), binder (1.6 wt %), tetra sodium pyrophosphate (0.5 wt %), and sodium saccharine (0.4 wt %) The test solution uses the following heating/cooling profile: hold for 5 minutes at 25° C., heat to 82° C., hold at 82° C. for 1 minute, cool to 25° C., and hold at 25° C. for 5 minutes.

Toothpaste Sample Preparation: Toothpaste compositions are prepared using the hot process by the following procedure:

(1) The binder is dispersed into the humectant with a high-speed stirrer and stirred for about 10 minutes.

(2) The water is heated to about 80° C. and added to the humectant/binder mixture with stirring continuing for 15 minutes while the temperature is maintained at 60-70° C.

(3) The dry ingredients, such as sodium saccharin, sodium benzoate, etc, exclusive of the abrasive are dry blended. The dry blend is stirred into the binder slurry and stirring is continued for 15 minutes while the temperature is maintained at 60-70° C.

(4) The resulting elixir is transferred to a low speed Ross mixer with a vacuum attachment. The Ross mixer is a double planetary gear, two-paddle mixer, which operates at 20 to 100 revolutions per minute and can be operated under vacuum.

(5) The abrasive is added to the elixir forming a paste and the paste is mixed for 15 minutes under vacuum (at least 720 mm Hg.).

(6) Flavoring is then added and the paste is mixed for 10 minutes in the Ross mixer under full vacuum.

(7) Surfactant, such as sodium lauryl sulfate (SLS), is then added and mixing of the paste is continued under vacuum for 20 minutes.

(8) A sample is withdrawn for testing, and the batch is discharged for filling tubes or other dispensers.

Toothpaste viscosity is measured with a T-Bar spindle E at 5 rpm using a Brookfield DVII Viscometer equipped with a Helipath attachment. The sample was first equilibrated at ambient temperature (25° C.). Viscosity was measured by placing the spindle directly into a tube containing 30-40 g of the toothpaste composition. The stationary spindle was positioned within the sample. The viscometer was turned on and readings were recorded every 10 seconds for a total period of 1 minute, for a total of six readings, which were then averaged.

Cuban Test—In the Cuban test (also termed the "Rack" test), the toothpaste is squeezed from a tube through a fixed orifice across a grid of parallel rods, adjacent pairs of rods of which are spaced apart at increasing distances from one another. The test results are expressed as the greatest space number (numbers are from 1-12) which represents the longest distance between rods that support the dentifrice ribbon without having it break. The rack is about 300 millimeters (mm) long and about 100 mm wide. The stainless steel rods are spaced at increasing distances apart starting at a spacing of 3 mm between rods 1 and 2 (space number 1). The distance between pairs of rods increases by 3 mm from pair to pair. Thus the distance between rods 2 and 3 is 6 mm, and the distance between the twelfth and thirteenth rods (space number 12) is 39 mm. For toothpastes that are not high moisture toothpastes, rack ratings or space numbers of 1-2 and 9-12 are not acceptable, rack ratings or space numbers of 3 and 8 are acceptable and rack ratings or space numbers of 4-7 are good. The Cuban test procedure is carried out as follows: (1) A nozzle with 3.2 mm diameter opening is fixed to a toothpaste tube filled with a toothpaste composition to be tested. (2) The tube filled with test toothpaste composition and having the nozzle attached is held at an angle of 45° to the rack device. Pressure is applied at the bottom of the tube and a uniform ribbon of paste is squeezed from the tube. While the ribbon of paste is extruded from the tube the tube is moved across the rack in a straight line. The time to stretch the ribbon of paste over the rack is usually about two to four seconds. If the ribbon breaks before the entire rack is traversed, the procedure is repeated. (3) The ribbon is allowed to stand for 30 seconds. At that time, the point or space number at which the ribbon breaks is recorded as the rack rating or Cuban value. (4) The test is performed three times and the average reading is recorded, rounding off to the nearest complete figure.

EXAMPLES

Example 1

Preparation of Co-Precipitated Carrageenan/Xanthan

Co-precipitated iota carrageenan/xanthan samples were prepared by pre-dissolving xanthan having a 1 wt % viscosity of 2800 cP and a pH of 7.3 in deionized water and subsequently adding the xanthan solution to an alkaline iota carrageenan solution. For samples 1-1 to 1-4, the xanthan was dissolved by dispersing in water to form a 0.5 wt % solution and heating to 82° C. with constant agitation. This xanthan solution was then combined with a 1.5 wt % iota carrageenan solution. (The hydrocolloid concentrations are based on the weight of a moisture-free, gum content basis for the hydrocolloid.) The two solutions were combined at equal volumes to provide a ratio of 7.5 parts of iota carrageenan to 25 parts of xanthan. The mixture was recovered by precipitation in 75% isopropyl alcohol/25% water, dried under heat and vacuum, then ground to a particle size of less than 100 mesh. Sample 1-5 was prepared in a similar manner except that the xanthan solution was prepared at a higher concentration of 0.8 wt % and 1 part of this xanthan solution was combined with 1.66 parts of a 1.5 wt % iota carrageenan to provide a ratio of 75 parts of iota carrageenan to 25 parts of xanthan. The dry co-precipitate was dissolved in deionized water and viscosity and pH was tested. The results are reported in Table 1.

TABLE 1

Co-precipitated carrageenan/xanthan (75:25 weight ratio, gum solids)

| | Xanthan | Iota Carrageenan | Viscosity of co-precipitated product (cP) | pH of co-precipitated product |
|---|---|---|---|---|
| 1-1 | Filtered | Filtered | 200 | 10.7 |
| 1-2 | Unfiltered | Unfiltered | 280 | 11.1 |
| 1-3 | Unfiltered | Filtered | 205 | 11.0 |
| 1-4 | Unfiltered | Filtered | 433 | 10.7 |
| 1-5 | Unfiltered | Filtered | 345 | 11.1 |

Example 2

Brabender Testing

Brabender hydration profiles were determined by measuring the viscosity response at a cup speed of 75 rpm during a temperature profile including both heating and cooling for a 2 weight % aqueous solution prepared using 490 grams of deionized water and 10 grams of the co-precipitated product from Example 1-3 or, as a comparative example, a 2 weight % aqueous solution prepared using 10 grams of a proportional "blend" of 75% carrageenan and 2.5% xanthan in 490 grams of deionized water (FIG. 1). The initial hydration profiles were very similar for both samples in deionized water at temperatures below about 40° C. During the heating stage, the co-precipitated product of the present invention exhibited a higher viscosity between 50° C. and 70° C. compared to the comparative "blend" sample. Similarly upon cooling, the co-precipitated material of the present invention was observed to provide a higher viscosity than the "blend" sample.

Figure 2:
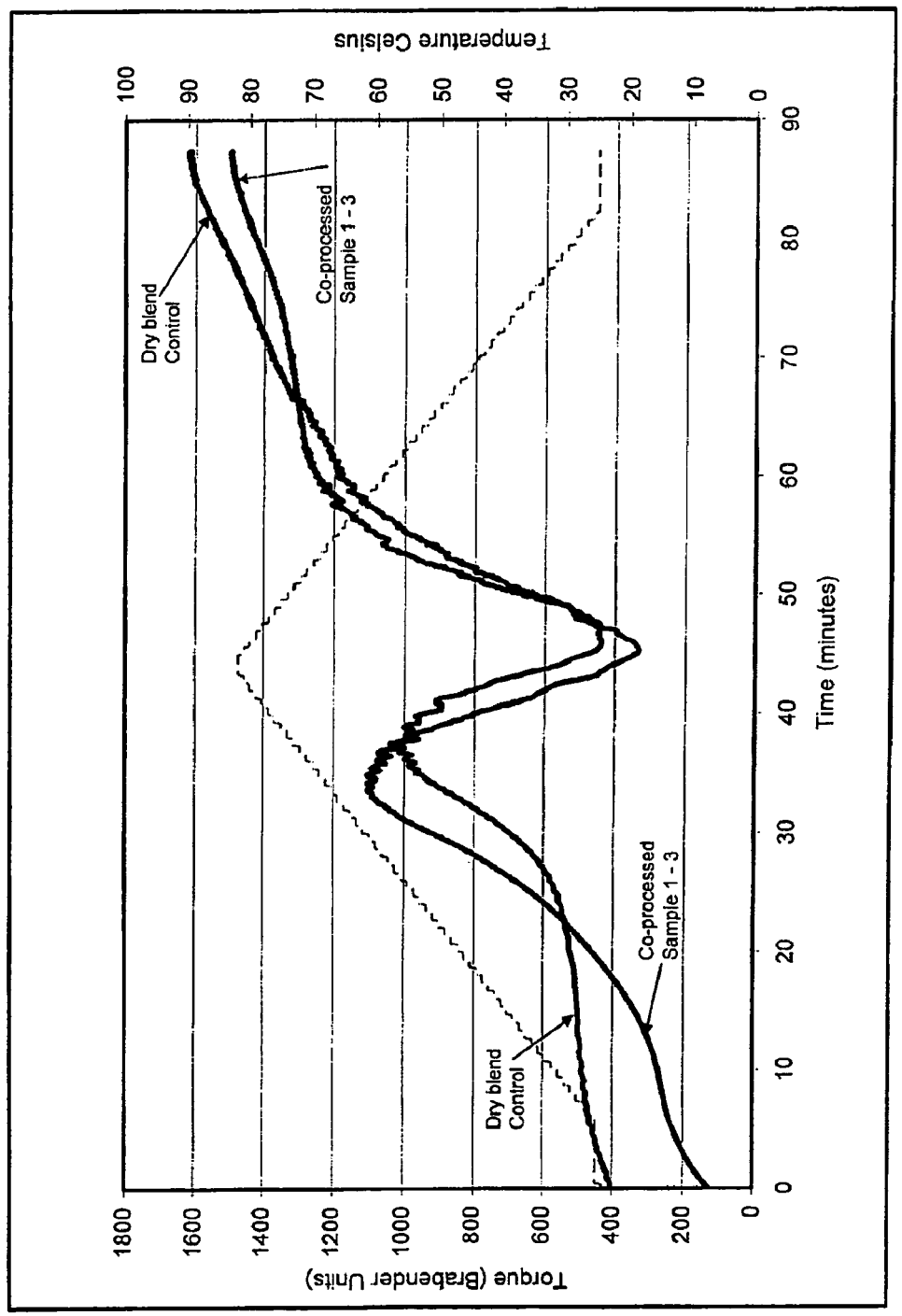
FIG. 2 shows Brabender hydration profiles for toothpaste elixirs with 1.6% by weight of a 75:25 weight ratio of co-precipitated iota carrageenan/xanthan (Example 1-3) and 1.6% by weight of a dry blend mixture of 75% iota carrageenan and 25% xanthan (comparative example), respectively

The hydration behavior of the co-precipitated sample of Example 1-3 and, as a comparative example, the proportional "blend" sample of 75 wt % carrageenan and 25 wt % xanthan were similarly characterized in a model toothpaste elixir containing 42.8 wt % de-ionized water, 33.1 wt % sorbitol, 19.5 wt % glycerin, 2.1 wt % sodium monofluorophosphate, 1.6 wt % of the sample, 0.5 wt % tetra sodium pyrophosphate, and 0.4 wt % of sodium saccharine (FIG. 2) prepared by the method described above.

Example 3

Drip Loss Comparison in Injected Fresh Pork Loin

Brine samples were prepared using 86.7 wt % water, 8.3 wt % salt (NaCl), 2.5 wt % sodium tripoly phosphate and 2.5 wt % sample, where the sample was one of iota carrageenan (non-inventive control), the co-precipitated 75:25 iota carrageenan/xanthan (sample 1-3 of the present invention) and, as a comparative example, a brine prepared using a proportional "blend" of 75 wt % iota carrageenan and 25 wt % xanthan. The brine solution viscosity was similar for the iota carrageenan (control) and the co-precipitated iota carrageenan/xanthan (sample 1-3) and the targeted injection was achieved for both.

TABLE 2

Viscosity of phosphate brines with a 75:25 co-precipitate ("cpt.") or with a dry blend ("blend")

|  | 5 rpm | 10 rpm | 50 rpm | 100 rpm |
| --- | --- | --- | --- | --- |
| 1.25% cpt. | 800 cP | 400 cP | 160 cP | 80 cP |
| 1.25% blend | 177,000 cP | 88,400 cP | 17760 cP | 8840 cP |
| 1.65% cpt. | 1600 cP | 800 cP | 240 cP | 120 cP |
| 1.65% blend | 178,000 cP | 89,200 cP | 18,080 cP | 9080 cP |
| 3.25% cpt. | 20,200 cP | 10,200 cP | 2240 cP | 1180 cP |
| 3.25% blend | 222,000 cP | 116,000 cP | 27040 cP | 14600 cP |

Brine viscosity was measured using Brookfield DVT III RT (spindle #7, 5° C.).

The brine solution prepared with the "blend" (comparative example) was more viscous, however, and somewhat difficult to pump. Sections of pork loins were injected with brine using a Fomaco FGM 20/80 injector equipped with eighty 3-mm pencil point needles to a target weight of 125% (the percentage of the weight after injection relative to the weight of the pork loins prior to injection), then weighed and placed on racks and re-weighed at intervals to obtain a weight loss as a function of time reported as drip loss (the drip loss is the percentage weight loss determined by measuring the remaining weight at a time after injection and comparing it to the weight of the pork loin immediately after injection).

Figure 3:
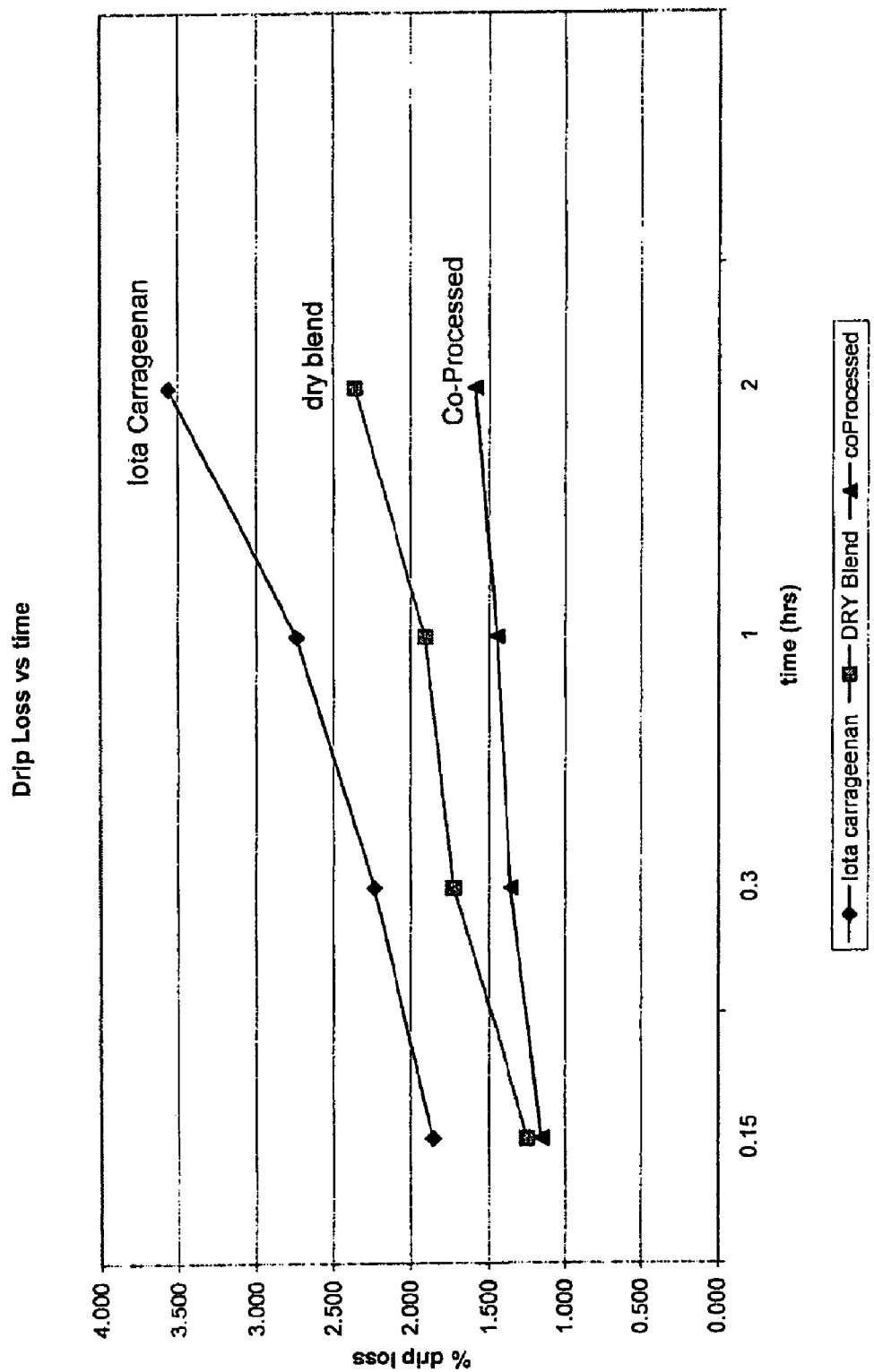
FIG. 3 shows drip loss as a function of time for uncooked pork loins after injection (target 125% of original weight) with brines containing 2.5% iota carrageenan (non-inventive control example), 2.5% of dry blend (75% iota carrageenan and 25% xanthan) (comparative example) or 2.5% of co-precipitated 75:25 iota carrageenan/xanthan (Example 1-3), respectively.
Figure 4:
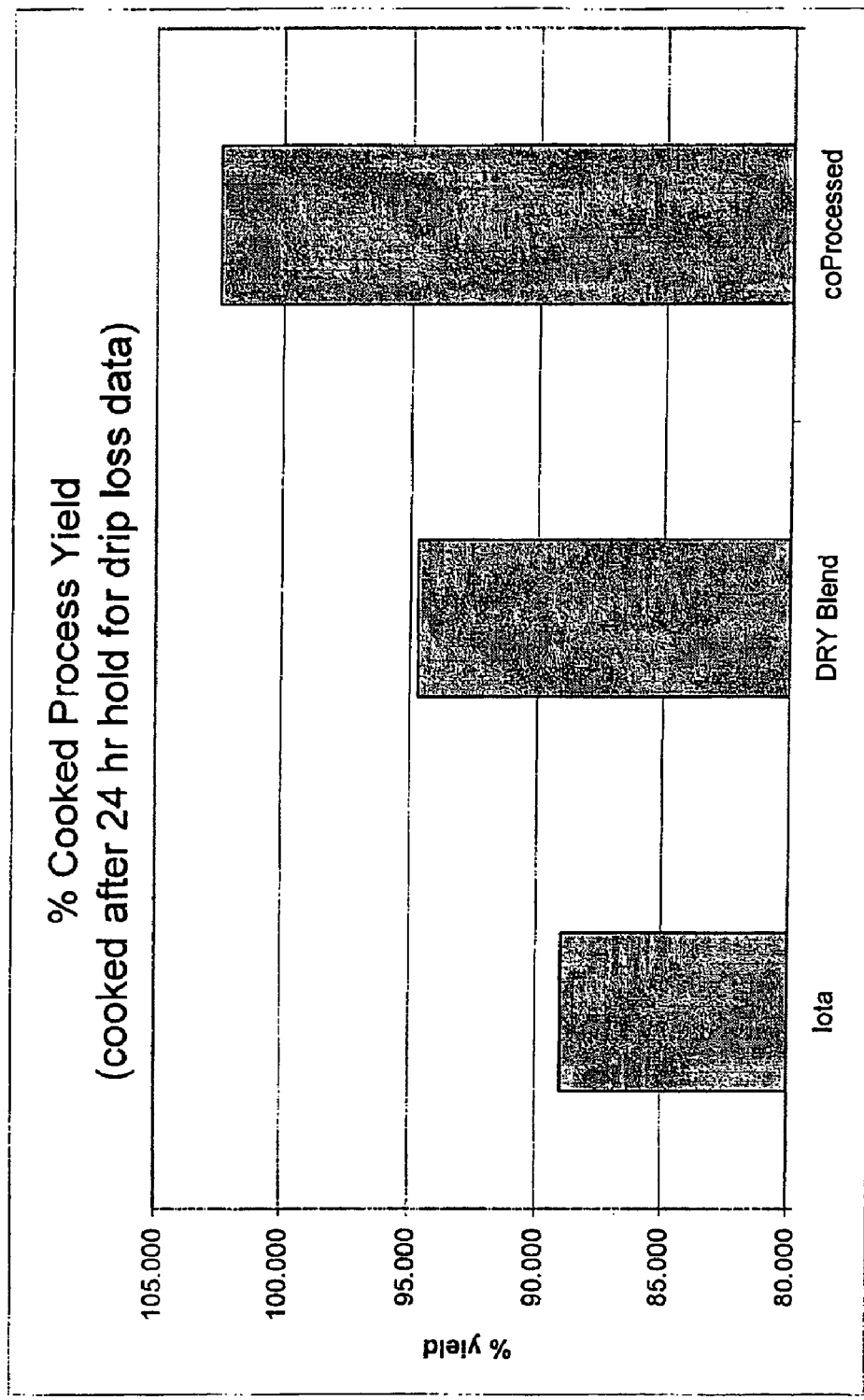
FIG. 4 shows the overall cooked process yield of pork loins cooked to an internal temperature of 165° F. (74° C.) that had been injected (target 125% of original weight) with brines containing 2.5% iota carrageenan (non-inventive control example), 2.5% of dry blend (75% iota carrageenan and 25% xanthan) (comparative example) or 2.5% of co-precipitated 75:25 iota carrageenan/xanthan (Example 1-3), respectively.

The average injection achieved using the brine prepared from the "blend" (comparative example) averaged 119%, which was somewhat lower than the 125% targeted injection level. As shown in FIG. 3, the drip loss of pork injected with a brine containing 2.5 wt % co-precipitated iota carrageenan/xanthan (example 1-3) showed reduced drip loss with time compared to the drip loss of pork injected with either a brine containing 2.5 wt % commercial iota carrageenan (non-inventive control example) or pork injected with a brine containing 2.5 wt % of the "blend" (comparative example). After 24 hours refrigerated hold for drip loss, the pork loins were cooked with a ramped heating to an internal temperature of 165° F. (74° C.). The overall cooked process yield, i.e., the final cooked weight less the initial weight (before injection) divided by the initial weight (before injection), is reported in FIG. 4. The highest cooked process yield was obtained for the pork loins which had been injected with brine using the brine containing the co-precipitated carrageenan/xanthan.

Example 4

Drip Loss Comparison in Injected Whole Chickens

The brine compositions used in Example 3 were injected into fresh whole chickens using a Fomaco FGM 20/80 injector equipped with eighty 3-mm pencil point needles to a target weight of 120%, then weighed and placed on racks and re-weighed at intervals to obtain a drip loss after fifteen minutes, thirty minutes, one hour, and two hours. The chickens were then covered and refrigerated and stored in a row of five stacked three high (per group of fifteen tested for each brine) to simulate shipment. The weight loss was measured after one, three, five, and seven days. The test was repeated in a second separate injection trial using a second batch of the same brines. In both cases, the brine prepared using the "blend" (comparative example) had a higher viscosity and could only be injected to a target weight of 115% as compared to a target weight of 120% which was achieved by injection of the brines using the iota carrageenan (non-inventive control example) and the co-precipitated blend of example 1-3, respectively. Table shows that the viscosity of phosphate brines prepared using the 75:25 co-precipitate vs. a dry blend composition are significantly lower in viscosity. The co-precipitate provides a desirable low viscosity with acceptable suspension at a range of concentrations. Processing advantages of using a lower viscosity brine include less plugging of injector needles, improved processability to reproducibly inject the same level, and more uniform distribution of brine within the meat (to avoid the formation of gel pockets).

Figure 5:
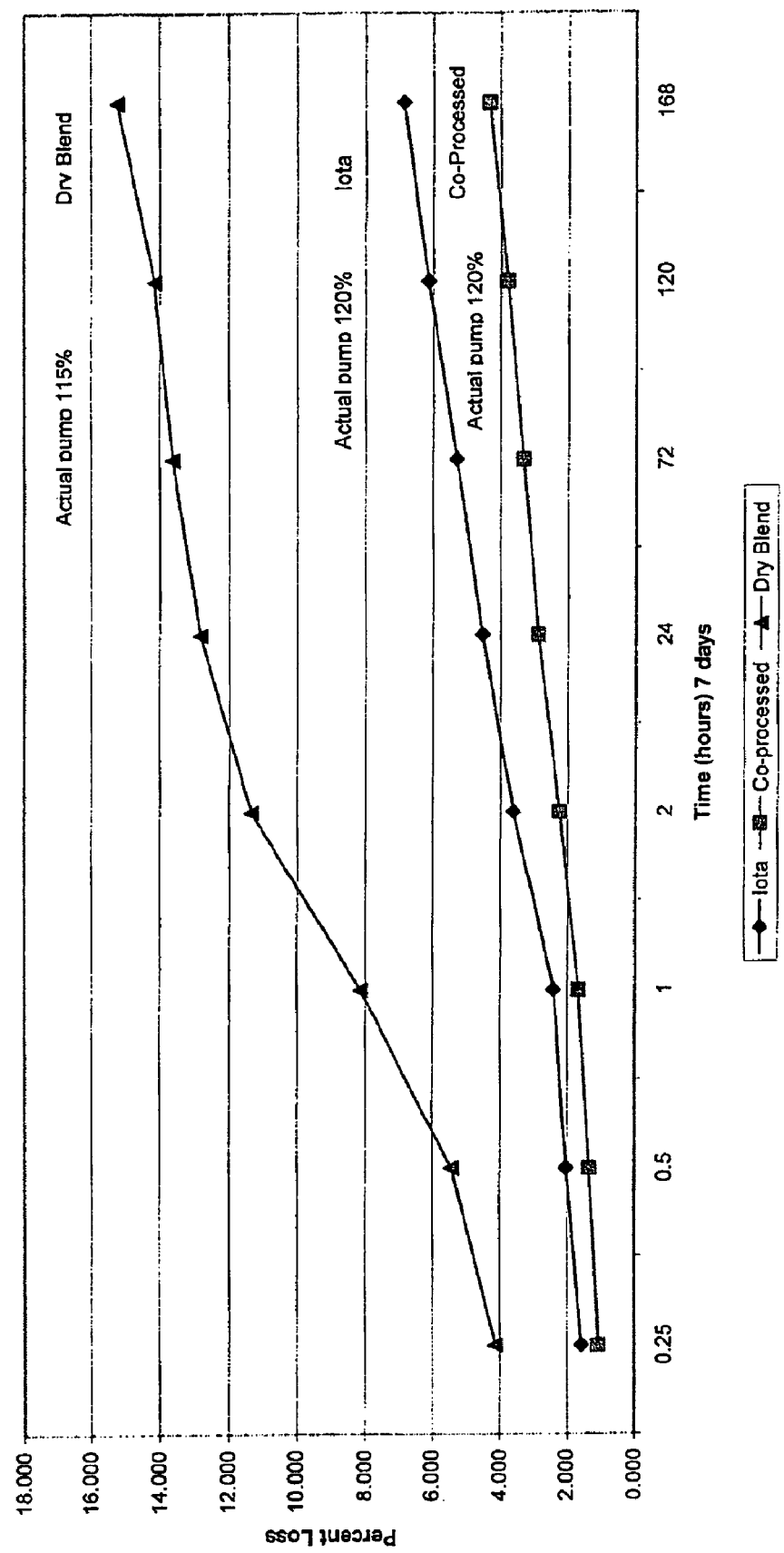
FIG. 5 shows drip loss as a function of time for uncooked whole chickens after injection (target 120% of original weight) with brines containing 2.5% iota carrageenan (non-inventive control example), 2.5% dry blend (75% iota carrageenan and 25% xanthan) (comparative example) or 2.5% of co-precipitated 75:25 iota carrageenan/xanthan (Example 1-3), respectively.
Figure 6:
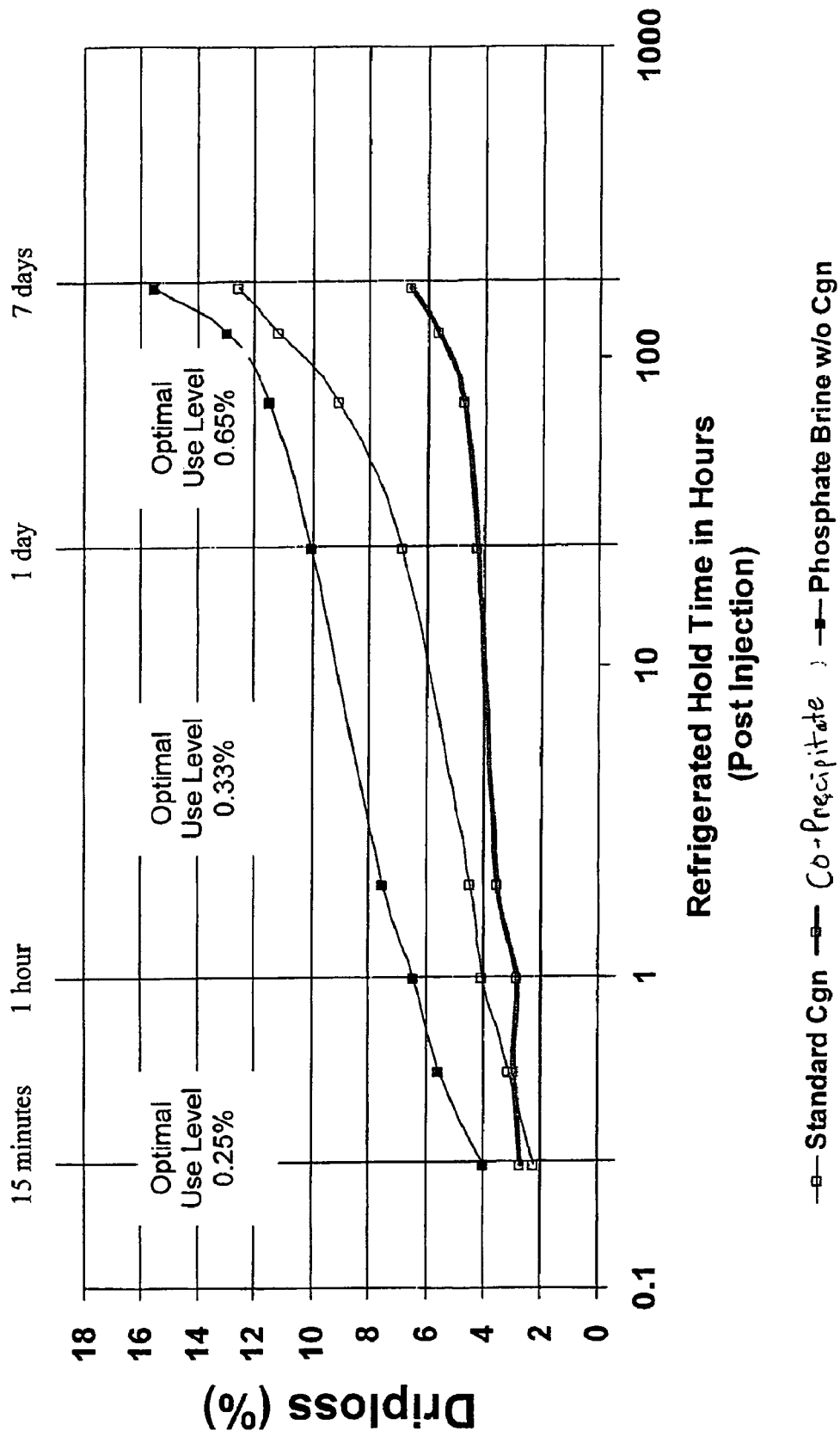
FIG. 6 shows drip loss (%) versus post-injection refrigerated time for brine injected fresh processed meats with a target injection level (extension level) of 125% of the weight of the meat immediately prior to injection using a co-precipitate (Brine B of Example 7) in accordance with the present invention, as well as comparative examples with a standard carrageenan-containing brine solution and a phosphate brine which did not contain carrageenan. This figure shows that the products of the invention can be customized for meat products that require different storage periods, thereby providing economic advantages, e.g. by reducing use levels for meats requiring shorter storage periods.
Figure 7:
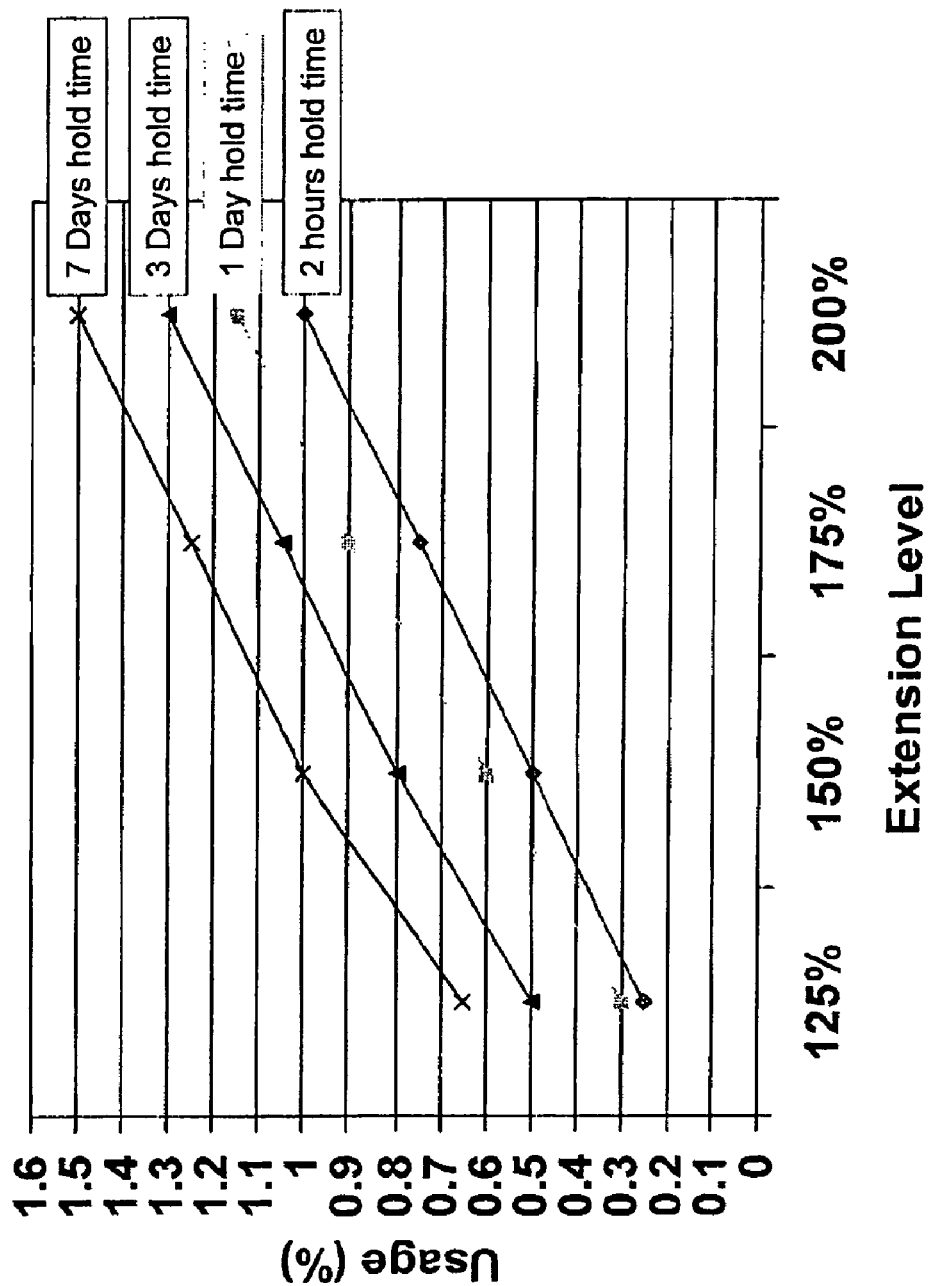
FIG. 7 shows hold times as a function of usage and extension levels for Brine B of Example 7 injected into fresh processed meats. Again, this shows the ability of the products of the invention to be customized by varying use levels for meats requiring storage periods of different lengths.
Figure 8:
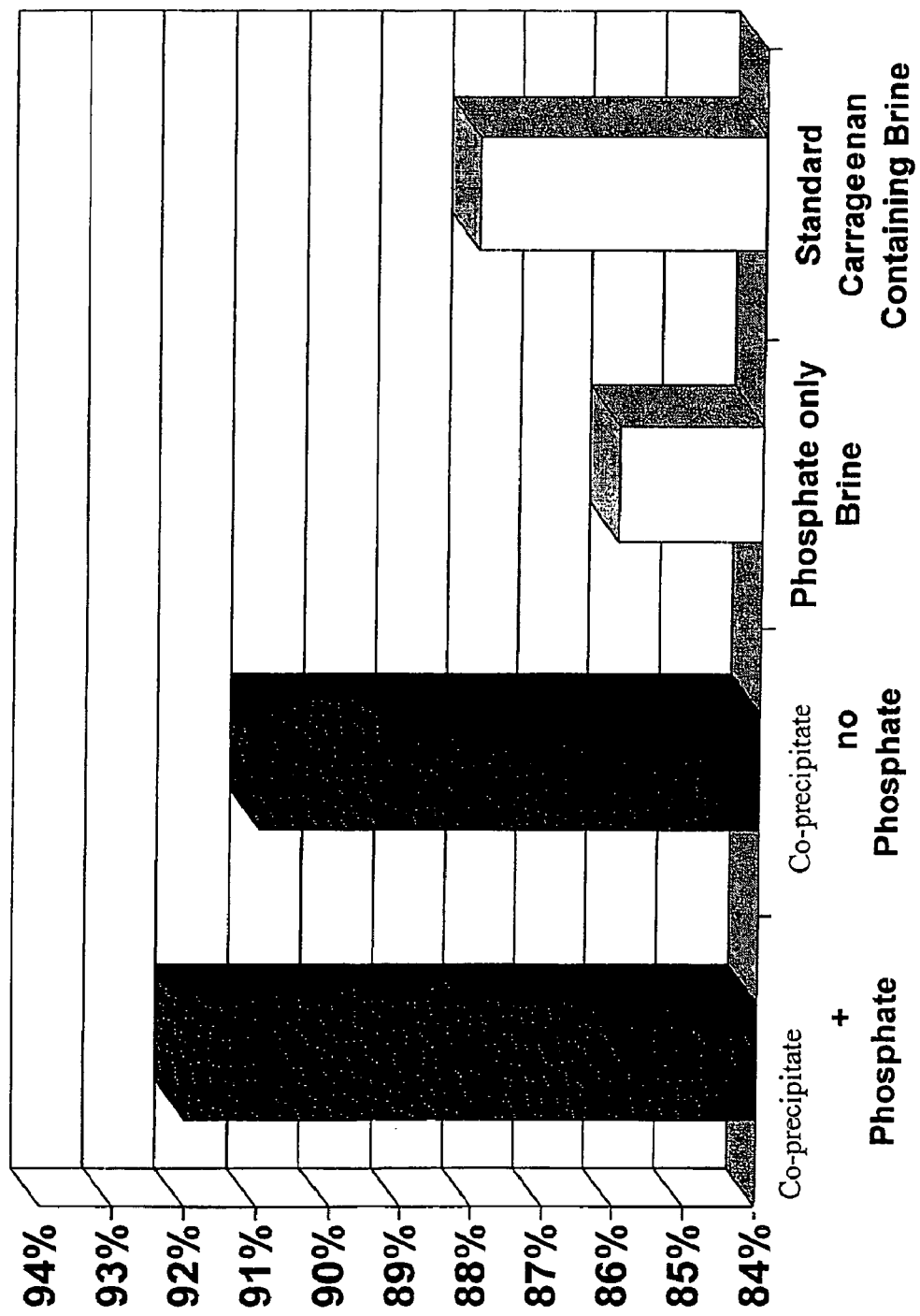
FIG. 8 shows cooking yields for brine injected fresh processed meats with a target injection level (extension level) of 125% of the weight of the meat immediately prior to injection using a co-precipitate (Brine B of Example 7) in accordance with the present invention with and without phosphates, as well as comparative examples with a standard carrageenan-containing brine solution and a phosphate brine which did not contain carrageenan.
Figure 9:
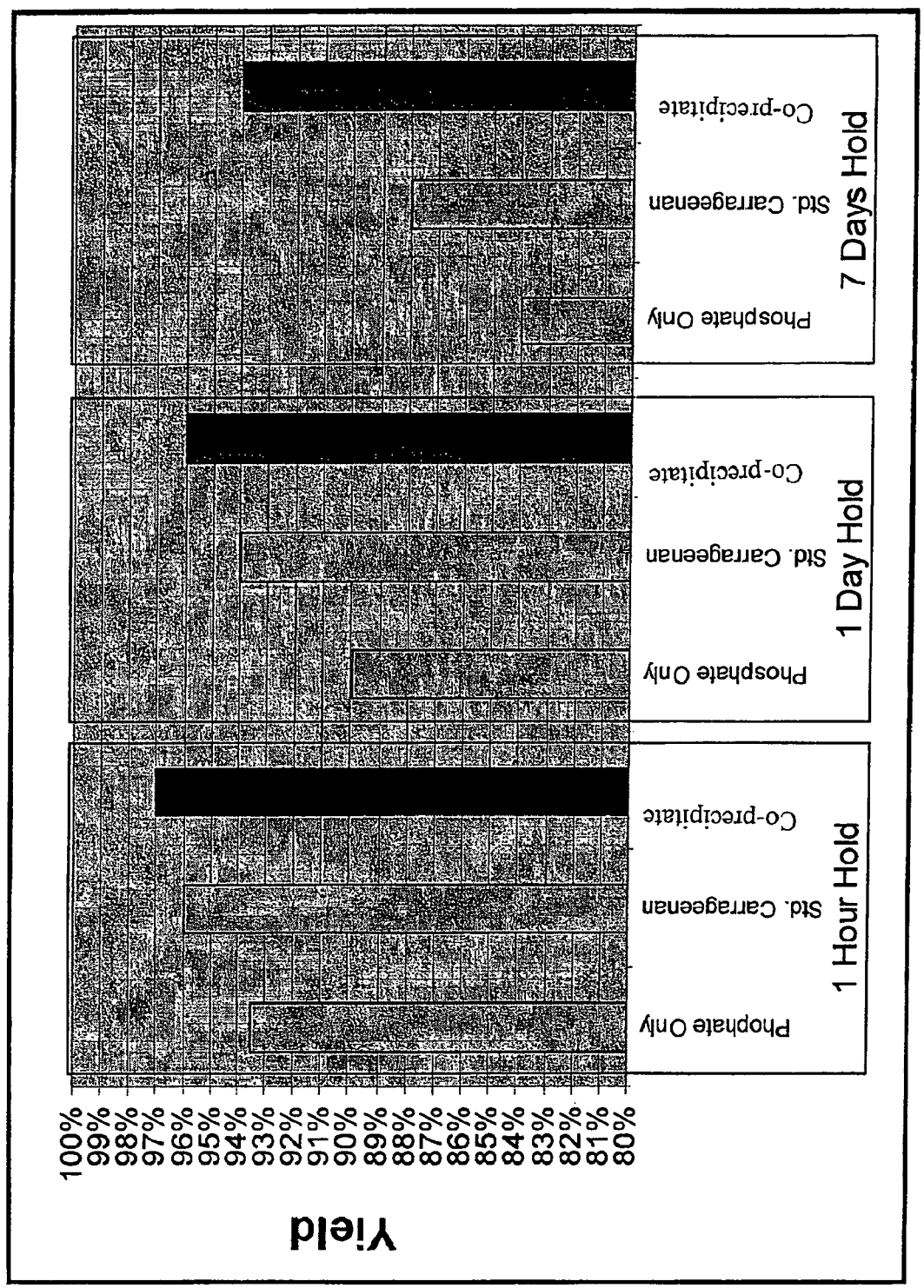
FIG. 9 shows comparative yields after different hold times for brine injected fresh processed meats with a target injection level (extension level) of 125% of the weight of the meat immediately prior to injection using a co-precipitate (Brine B of Example 7) in accordance with the present invention, as well as comparative examples with a standard carrageenan-containing brine solution and a phosphate brine which did not contain carrageenan.
Figure 10:
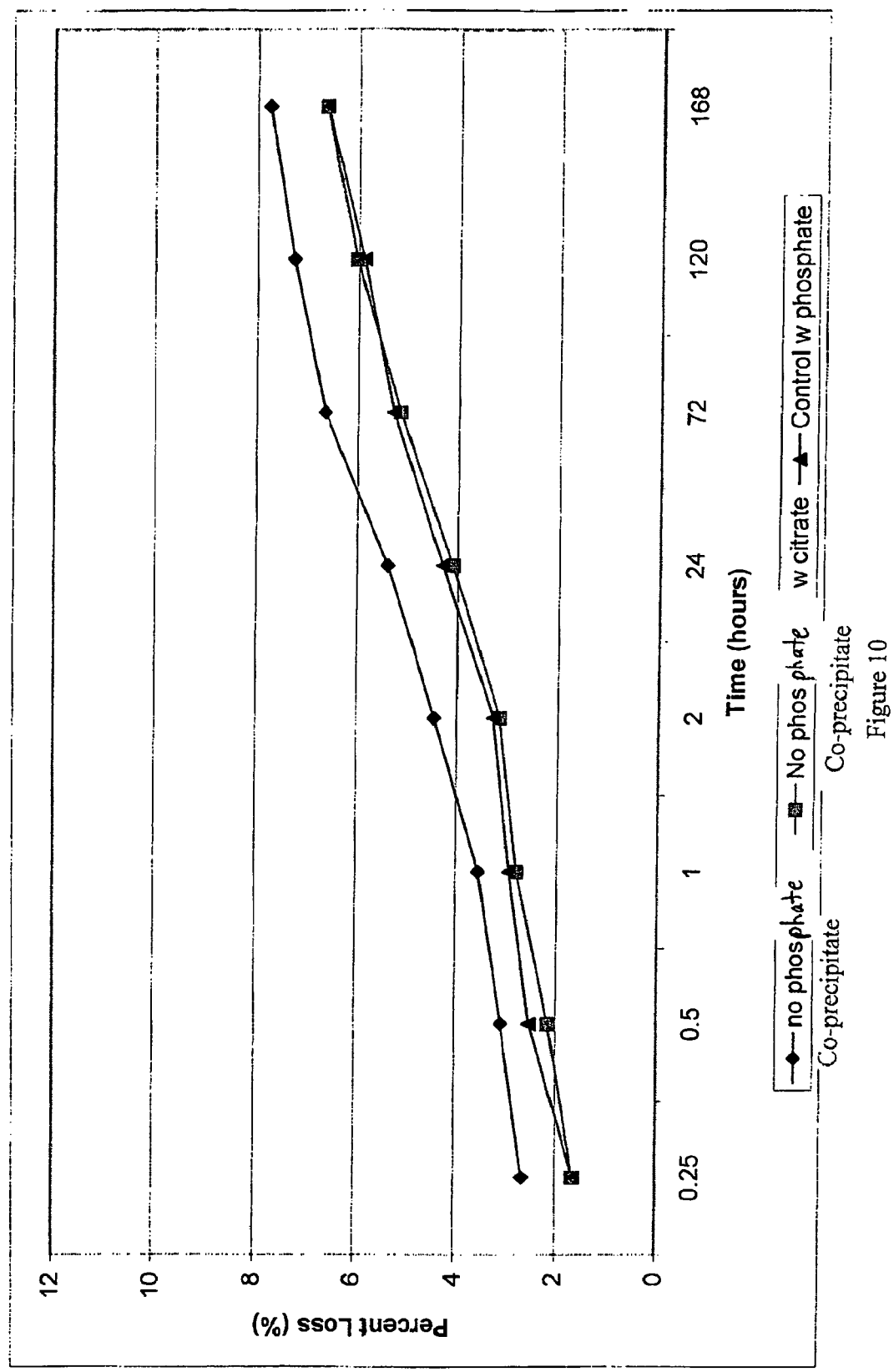
FIG. 10 shows the ability to replace phosphates in brine solutions with a brine solution containing a co-precipitate according to the present invention (Brine B of Example 7) and containing sodium citrate in terms of comparative yields (percent loss of weight) over time.

As shown in FIG. 5, which shows the average of the two trials, the drip loss of chicken injected with a brine containing 2.5 wt % co-precipitated iota carrageenan/xanthan (example 1-3) showed the lowest drip loss with time when compared to the drip loss of chicken injected with the brine containing 2.5 wt % commercial iota carrageenan (non-inventive control example) and the drip loss of chicken injected with a brine prepared using 2.5 wt % of the "blend" (comparative example). After seven days, the drip loss for injected brines containing the co-precipitated sample (example 1-3) showed a significant advantage since the drip loss was 2.25% lower than the drip loss for the chickens injected with the brine containing only iota carrageenan (non-inventive control example) and 11% lower than for the chickens injected with the brine containing the "blend" (comparative example).

Example 5

Co-Precipitates of Xanthan with Different Types of Carrageenans

Aqueous solutions were prepared with the following hydrocolloids: kappa carrageenan with a 1.5 wt % viscosity of 22 cP and pH=9.1; iota carrageenan with a 1.5 wt % viscosity of 30 cP and a pH=9.1; lambda carrageenan with a viscosity of 105 cP and a pH of 8.7; iota carrageenan with a 1.5 wt % viscosity of 38 cP and a pH of 10); and a xanthan with a 1 wt % viscosity of 2800 cP and a pH of 7.3. Mixtures at specific weight ratios were prepared by dispersing the carrageenan and xanthan in water at appropriate ratios to provide 1.75% to 2.0% solids content at room temperature. Samples were heated to 90° C. with mixing. If required, the pH was adjusted to within the range of 8 to 10 with a 10% solution of sodium hydroxide. After 1 hour of mixing, the co-precipitate was recovered by co-precipitation in an isopropyl alcohol/water solution, dried and ground to a particle size of less than 100 mesh. The dry co-precipitate was tested for viscosity, pH, and gel strength (as reported in Table 3) and for acid resistance compared to a dry blend mixture of the same composition (as reported in Table 4). The acid resistance as determined by viscosity loss at pH 3.8 is superior for the co-precipitate compared to the dry blend. In addition, the results of Table 3 illustrate the formulating flexibility provided by the present compositions as can be seen, for example, by the fact that a 90:10 composition can be a liquid in a milk gel. "NT" indicates "not tested."

TABLE 3

Gel Properties of Co-precipitated Xanthan Gum with Various Carrageenans

| | 3A | 3B | 3C | 3D | 3E | 3F | 3G |
|---|---|---|---|---|---|---|---|
| Co-precipitate Components | | | | | | | |
| Carrageenan (Cgn) type | Kappa (22 cP) | Iota (30 cP) | Lambda (105 cP) | Iota (41 cP) | Iota (38 cP) | Iota (38 cP) | Iota (38 cP) |
| Carrageenan to xanthan ratio | 75:25 | 75:25 | 75:25 | 75:25 | 90:10 | 75:25 | 60:40 |
| Solids before precipitation (%) | 2.0 | 2.0 | 2.0 | 1.75 | 2.0 | 1.75 | 2.0 |
| Viscosity before precipitation (cP) | 960 | 1080 | 1640 | 295 | 600 | 550 | 130 |
| Co-precipitate Solution Properties | | | | | | | |
| Percent Moisture | 3.63% | 6.93% | 5.95% | 11.74% | NT | NT | NT |
| 1.5 wt % viscosity (cP) | 380 | 430 | 542 | 265 | 700 | 270 | 105 |
| pH | 7.1 | 9.9 | 8.6 | 9.7 | 9.3 | 9.3 | 8.8 |
| 2% water gel | 96 gf, 0.9 cm | 97 gf, 2.2 cm | Fluid | 32 gf, 2.1 cm | 44 gf 2.0 cm | 42 gf 2.1 cm | 54 gf, 2.1 cm |
| 1% + 1 water gel | 249 gf, .22 cm | 108 gf, 1.8 cm | Fluid | 82 gf, 1.9 cm | 71 gf, 1.9 cm | 89 gf, 1.9 cm | 122 gf, 1.9 cm |
| 1% + 1 + 1 water gel | 323 gf, .22 cm | 120 gf, 2.1 cm | 52 gf, 2.1 cm | 116 gf, 2.0 cm | NT | NT | NT |
| milk gel | 50 gf, 0.4 cm | 62 gf, 1.1 cm | Fluid | 22 gf, .67 cm | Fluid | 34 gf, 0.6 cm | 71 gf, 1.1 cm | gf = grams force exerted by the metal plunger

TABLE 4

Acid Resistance of Co-precipitates vs. Corresponding Dry Blend Compositions

| Co-precipitate | 3A | 3B | 3C | 3D |
|---|---|---|---|---|
| Carrageenan type | Kappa (22 cP) | Iota (30 cP) | Lambda (105 cP) | Iota (41 cP) |
| Carrageenan to Xanthan Ratio (wt) | 75:25 | 75:25 | 75:25 | 75:25 |
| Acid resistance of Dry Blend* | −1.3 | −2.0 | −2.9 | −1.7 |
| Acid resistance of Co-precipitate* | 0 | −1.2 | −1.8 | −1.0 |

*hydrolysis rate indicated as cP/minute (×1000)

Example 6

Xanthan was dispersed at about 1 wt % in water using a high shear mixer. The xanthan solution and an alkaline carrageenan solution were metered into a continuous stirred tank at rates sufficient to produce 1.0 to 1.5% solids mixtures of 75% carrageenan and 25% xanthan or 90% carrageenan and 10% xanthan. The solution was subsequently evaporated to slightly concentrate the solids, then coagulated in a mixture of isopropyl alcohol and water, centrifuged, pressed and vacuum dried to remove the alcohol, batch dried to a moisture content of below 5% and ground to a particle size less than 100 mesh.

TABLE 5

Properties of Carrageenan/Xanthan Co-precipitates

| | Sample | | |
|---|---|---|---|
| | 21 | 22 | 23 |
| Carrageenan (%) | 90 | 74 | 75 |
| 1.5 wt % viscosity (cP) | 36 | 60 | 44 |
| 1.5 wt % pH | 8.8 | 8.6 | 8.7 |
| % through 100 Mesh | 99.8 | 99.7 | 99.8 |
| Milk Gel | 69 | 64 | 53 |
| Mean particle size (micrometers) | 79 | 87 | 33 |
| Median particle size (micrometers) | 75 | 78 | 18 |

Example 7

Drip Loss Comparison in Injected Whole Chicken

The following brines were prepared, with all percentages by weight:

Brine A: 88.75% water, 7.5% sodium chloride, 2.5% sodium tripolyphosphate and 1.25% of co-precipitate with a 75:25 ratio by weight carrageenan to xanthan Brine B: 88.75% water, 7.5% sodium chloride, 2.5% sodium tripolyphosphate 0.375% of sodium carbonate and 0.875% of co-precipitate with a 75:2.5 ratio by weight carrageenan to xanthan Brine C: 88.75% water, 7.5% sodium chloride, 1.875% dextrose, 0.625% sodium citrate, 0.375% of sodium carbonate and 0.875% of co-precipitate with a 75:25 ratio by weight carrageenan to xanthan Brine D: 88.75% water, 7.5% sodium chloride, 2.5% dextrose, 0.375% of sodium carbonate and 0.875% of co-precipitate with a 75:25 ratio by weight carrageenan to xanthan.

Fresh three pound whole chickens were injected with brine using a Fomaco FGM 20/80 injector equipped with eighty 3-mm pencil point needles to about ~120% (vs. a target of 12.5% where 100% corresponds to the weight of meat prior to injection), weighed to determine amount of brine injected, placed on racks and re-weighed at intervals to obtain a drip loss after fifteen minutes, thirty minutes, one hour, and two hours. The chickens were then covered and refrigerated, stored in a row of five stacked three high (per group of fifteen tested for each brine) to simulate shipment.

TABLE 6

Drip Loss versus Time

| | Sample | | |
|---|---|---|---|
| | 22 | Pilot sample | 22' |
| Brine injected (%) | 21.1 | 21.6 | 21.8 |
| 15 minutes (% loss) | 1.96 | 1.78 | 1.41 |
| 30 minutes (% loss) | 3.13 | 3.05 | 2.17 |
| 1 hour (% loss) | 4.14 | 3.84 | 3.44 |
| 2 hour (% loss) | 4.64 | 4.44 | 4.43 |
| 1 day (% loss) | 6.01 | 5.60 | 5.16 |
| 3 days (% loss) | 7.15 | 6.71 | 6.79 |
| 5 days (% loss) | 8.63 | 7.90 | 7.58 |
| 7 days (% loss) | 9.39 | 9.31 | 8.66 |
| Cook yield after 7 days | 87.8% | 90.9% | 90.7% |

TABLE 7

Drip Loss versus Time

| | Sample | | |
|---|---|---|---|
| | 23 | Pilot sample | 23' |
| Brine injected (%) | 20.8 | 20.2 | 20.7 |
| 15 minutes (% loss) | 1.71 | 1.46 | 1.16 |
| 30 minutes (% loss) | 2.90 | 2.43 | 1.96 |
| 1 hour (% loss) | 3.91 | 3.15 | 2.42 |
| 2 hour (% loss) | 4.66 | 3.91 | 3.10 |
| 1 day (% loss) | 5.43 | 4.53 | 4.24 |
| 3 days (% loss) | 6.14 | 6.51 | 5.76 |
| 5 days (% loss) | 7.39 | 7.30 | 6.68 |
| 7 days (% loss) | 9.76 | 9.22 | 9.10 |
| Cook yield after 7 days | 88.6% | 88.8% | 90.4% |

TABLE 8

Drip Loss versus Time

| | Sample | | |
|---|---|---|---|
| | 23 No phosphate | 23 No phosphate or citrate | 23 phosphate |
| Brine injected (%) | 23.6 | 20.5 | 20.1 |
| 15 minutes (% loss) | 2.64 | 1.64 | 1.64 |
| 30 minutes (% loss) | 3.08 | 2.15 | 2.51 |
| 1 hour (% loss) | 3.56 | 2.79 | 2.93 |
| 2 hour (% loss) | 4.45 | 3.14 | 3.28 |
| 1 day (% loss) | 5.39 | 4.10 | 4.30 |
| 3 days (% loss) | 6.65 | 5.16 | 5.30 |
| 5 days (% loss) | 7.29 | 6.03 | 5.88 |
| 7 days (% loss) | 7.77 | 6.64 | 6.63 |
| Cook yield after 7 days | 90.7% | 90.9% | 87.8% |

% loss is the percentage of the weight lost relative to the initial injected weight The terms and expressions which have been employed are used as terms of description and not of limitation. There is no intention in the use of such terms and expressions of excluding any equivalents of the features shown and described or portions thereof. It is recognized, therefore, that various modifications are possible within the scope and spirit of the invention. Accordingly, the invention incorporates variations that fall within the scope of the following claims.

What is claimed is:

1. An aqueous composition comprising a co-precipitate hydrocolloid composition consisting essentially of at least one carrageenan comprising iota carrageenan or kappa carrageenan and at least one xanthan, wherein said carrageenan to xanthan ratio is from 60:40 to 95:5, based on weight percentage.

2. The aqueous composition as claimed in claim 1, wherein the co-precipitate consists of at least one said carrageenan and at least one xanthan, wherein said carrageenan to xanthan ratio is from 60:40 to 95:5, based on weight percentage.

3. The aqueous composition of claim 2, wherein said carrageenan to xanthan ratio is from 60:40 to 90:10, based on weight percentage.

4. The aqueous composition of claim 2, wherein said carrageenan to xanthan ratio is from 70:30 to 80:20, based on weight percentage.

5. The aqueous composition of claim 2, wherein said carrageenan to xanthan ratio is about 75:25, based on weight percentage.

6. The aqueous composition of claim 1, wherein said carrageenan comprises kappa carrageenan.

7. The aqueous composition of claim 1, wherein said carrageenan is iota carrageenan.

8. A process for treating an uncooked food product comprising at least one of meat, seafood and poultry, comprising the step of adding to the uncooked food product the aqueous composition of claim 1.

9. A process for treating an uncooked food product comprising at least one of meat, seafood and poultry, comprising the step of adding to the uncooked food product the aqueous composition of claim 2.

10. A process as claimed in claim 8, wherein the food product comprises meat.

11. A process as claimed in claim 8, wherein the food product comprises seafood.

12. A process as claimed in claim 8, wherein the food product comprises poultry.

13. A process as claimed in claim 8, wherein the aqueous composition is added by injection.

14. A process as claimed in claim 8, wherein said carrageenan is iota carrageenan.

* * * * *